US007579440B2

(12) United States Patent
Timans et al.

(10) Patent No.: US 7,579,440 B2
(45) Date of Patent: Aug. 25, 2009

(54) MAMMALIAN CYTOKINES; RELATED REAGENTS

(75) Inventors: Jacqueline C. Timans, Mountain View, CA (US); Stefan Karl-Heinz Pflanz, Munich (DE); Robert A. Kastelein, Redwood City, CA (US); J. Fernando Bazan, Palo Alto, CA (US); Donna Rennick, Los Altos, CA (US); Rene de Waal Malefyt, Sunnyvale, CA (US); Jeanne Cheung, Belmont, CA (US)

(73) Assignee: Schering Corporation, Kenilworth, NJ (US)

( * ) Notice: Subject to any disclaimer, the term of this patent is extended or adjusted under 35 U.S.C. 154(b) by 579 days.

(21) Appl. No.: 10/777,790

(22) Filed: Feb. 11, 2004

(65) Prior Publication Data
US 2004/0198955 A1    Oct. 7, 2004

Related U.S. Application Data

(60) Division of application No. 10/000,776, filed on Nov. 30, 2001, now Pat. No. 7,148,330, which is a continuation-in-part of application No. 09/791,497, filed on Feb. 22, 2001, now abandoned, which is a continuation-in-part of application No. 09/627,897, filed on Jul. 27, 2000, now abandoned.

(60) Provisional application No. 60/147,763, filed on Aug. 6, 1999, provisional application No. 60/146,581, filed on Jul. 30, 1999.

(51) Int. Cl.
C07K 14/00    (2006.01)
(52) U.S. Cl. .......................... 530/351; 530/350; 435/41
(58) Field of Classification Search ........................ None
See application file for complete search history.

(56) References Cited

U.S. PATENT DOCUMENTS

| 6,165,461 | A    | 12/2000 | Cobb et al. |
| 6,632,624 | B1   | 10/2003 | Degorce et al. |
| 6,822,082 | B2 * | 11/2004 | Sheppard et al. ........... 536/23.1 |

FOREIGN PATENT DOCUMENTS

| WO | WO 94/01548 A2 | 1/1994 |
| WO | WO 01/70986 A2 | 9/2001 |

OTHER PUBLICATIONS

Benjamini et al., "Antigencity" Immunology, A Short Course, 2nd ed., 1992 (John Wiley & Sons, Inc.), p. 40.
Riechmann et al. (1988) *Nature* 332:323-327 "Reshaping human antibodies for therapy".
Paulina Balbas and Francisco Bolivar, *Methods in Enzymology*, 185:14-37, 1990. "[3] Design and Construction of Expression Plasmid Vectors in *Escherichia coli*".
J. Fernando Bazan, et al., *Nature*, 379:591, Feb. 15, 1996. "A newly defined interleukin-1?".
S.L. Beaucage and M.H. Caruthers, *Tetrahedron Letters*, 22(20):1859-1862, 1981, "Deoxynucleoside Phosphoramidites—A New Class of Key Intermediates for Deoxypolynucleotide Synthesis".
M.F. Bonaldo, et al., *GenBank*, Accession No. AA875330, Jul. 4, 1999. Definition: "Ul-R-E0-cn-h-10-0-Ul.s1 Ul-R-E0 Rattus norveglcus cDNA clone Ul-R-E0-cn-h-10-0-Ul 3' similar to gi|2947051|gb|AC002425|HUAC002425 Homo sapiens Chromosome 16 BAC clone CIT987SK-A-575C2, complete sequence [Homo sapiens], mRNA sequence".
Qi Chen, et al., *Nature*, 407:916-920, Oct. 19, 2000. "Development of Th1-type immune responses require the type 1 cytokine receptor TCCR".
Q. Chen, et al., *GenBank*, Accession No. AF265242, Oct. 29, 2000. Definition: "Homo sapiens type-l T cell cytokine receptor mRNA, complete cds..".
Andreas D. Christ, et al., *Gastroenterology*, 115:307-313, 1998. "An Interleukin 12-Related Cytokine is Up-regulated in Ulcerative Colitis but Not in Crohn's Disease".
Odile Devergne, et al., Proc. Natl. Acad. Sci. USA, 94:12041-12046, Oct. 1997. "Epstein-Barr virus-induced gene 3 and the p35 subunit of Interleukin 12 form a novel heterodimeric hematopoietin".
Odile Devergne, et al., *GenBank*, Accession No. NM_005755, Jun. 29, 2001. Definition: "Homo sapiens Epstein-Barr virus induced gene 3 (EBI3), mRNA."
Alan D. Elbein, *Ann. Rev. Biochem.*, 56:497-534, 1987. "Inhibitors of the Biosynthesis and Processing of N-Linked Oligosaccharide Chains".
Maurice K. Gately, et al., *Annu. Rev. Immunol.*, 16:495-521, 1998. "The Interleukin-12/Interleukin-12-Receptor System: Role in Normal and Pathologic Immune Responses".
Herve Groux, et al., *J. Exp. Med.*, 184:19-29, Jul. 1996. "Interleukin-10 Induces a Long-Term Antigen-specific Anergic State in Human CD4+ T Cells".
Shin-ichi Hashimoto, et al., *Immunobiology*, 96(6):2206-2214, Sep. 15, 2000. "Identification of genes specifically expressed in human activated and mature dendritic cells through serial analysis of gene expression."
Sten Eric W. Jacobsen, *The Cytokine Handbook*, 3rd ed., Ch 13:365-367, Academic Press Ltd., 1998, "Interleukin-11: A Cytokine Signaling Through gp130 with Pleiotropic Effects and Potential Clinical Utility Within and Outside the Hematopoietic System".
Ross D. King and Michael J.E. Sternberg, *Protein Science*, 5:2298-2310, 1996. "Identification and application of the concepts important for accurate and reliable protein secondary structure prediction".
Thomas A. Kunkel, et al., *Methods in Enzymology*, 154:367-382, 1987. "Rapid and Efficient Site-Specific Mutagenesis without Phenotypic Selection".
B.J. Loftus, et al., *GenBank*, Accession No. AC002544, Nov. 23, 1999. Definition: "Homo sapiens Chromosome 16 BAC clone CIT987SK-A-761H5, complete sequence".

(Continued)

Primary Examiner—Dong Jiang
(74) Attorney, Agent, or Firm—Schering-Plough Patent Dept.

(57) ABSTRACT

Purified genes encoding a cytokine or composite cytokine from a mammal, reagents related thereto including purified proteins, specific antibodies, and nucleic acids encoding these molecules are provided. Methods of using said reagents and diagnostic kits are also provided.

3 Claims, 3 Drawing Sheets

OTHER PUBLICATIONS

Loftus, B.J., et al., "Genome duplications and other features in 12 Mb of DNA sequence from human chromosome 16p and 16q", Database GenEmbl on STN, Loculs HUAC002544 (GenEmbl, Nov. 23, 1999).

Verne A. Luckow and Max D. Summers, *Bio/Technology*, 6:47-55, Jan. 1988. "Trends in the Development of Baculovirus Expression Vectors".

M. Marra, et al., *GenBank*, Accession No. AA266872, Mar. 21, 1997. Definition: "mz93e09.r1 Soares mouse lymph node NbMLN Mus musculus cDNA clone Image:721000 5', mRNA sequence".

NCI-CGAP, *GenBank*, Accession No. AI085007, Aug. 28, 1998. Definition: "ow88d07.s1 Soares_fetal_liver_spleen_1NFLS_S1 Homo sapiens cDNA clone Image:1653901 3' similar to contains element MER22 repetitive element ;, mRNA sequence".

Saul B. Needleman and Christian D. Wunsch, *J. Mol. Biol.*, 48:443-453, 1970. "A General Method Applicable to the Search for Similarities in the Amino Acid Sequence of Two Proteins".

Birgit Oppmann, et al., *Immunity*, 13:715-725, Nov. 2000. "Novel p19 Protein Engages IL-12p40 to Form a Cytokine, IL-23, with Biological Activities Similar as Well as Distinct from IL-12".

Patricia Parnet, et al., *Journal of Biological Chemistry*, 271(8):3967-70, 1996. "L-1Rrp is a Novel Receptor-like Molecule Similar to the Type I Interleukin-1 Receptor and Its Homologues T1/ST2 and IL-1R AcP".

Steven A. Rosenberg, *Journal of Clinical Oncology*, 10(2):180-199, Feb. 1992. "The Immunotherapy and Gene Therapy of Cancer".

Burkhard Rost and Chris Sander, *Proteins: Structure, Function and Genetics*, 19:55-72, 1994. "Combining Evolutionary Information and Neural Networks to Predict Protein Secondary Structure".

Martin A. Schwartz, et al., *J. of Immunotherapy*, 16:95-104, 1994. "Stimulation of Cytokine Activity by Interleukin-10".

Julie D. Thompson, et al., *Nucleic Acids Research*, 25(24):4876-4882, 1997. "The CLUSTAL_X windows interface: flexible strategies for multiple sequence alignment aided by quality analysis tools".

Giorgio Trinchieri, *Annu. Rev. Immunol.*, 13:251-276, 1995. "Interleukin-12: A Proinflammatory Cytokine With Immunoregulatory Functions That Bridge Innate Resistance And Antigen-Specific Adaptive Immunity".

Giorgio Trinchieri, *Advances In Immunology.*, 70:83-243, 1998. "Interleukin-12: A Cytokine at the interface of Inflammation and Immunity".

Jean Viallet and John D. Minna, *Progress in Growth Factor Research*, 1:89-87, 1989. "Gastrin-Releasing Peptide (GRP, Mammalian Bombesin) In The Pathogenesis Of Lung Cancer".

Slobodan Vukicevic, et al., *Proc. Natl., Acad. Sci. USA*, 93:9021-26, Aug. 1996. Induction of Nephrogenic Mesenchyme by Osteogenic Protein 1 (bone morphogenetic protein 7).

Meir Wilchek, et al., *Methods In Enzymology*, 104:3-55, 1984. "[1] affinity Chromatography".

\* cited by examiner

```
2    1 QDLENNPKIGLSLLLLPLLLVQAGVWGFPRPPGRPQLSLQELRREFTVS            49
6    1 MGQTAGDLGWRLSLLLLPLLLVQAGVWGFPRPPGRPQLSLQELRREFTVS            50
       ************************************************

2   50 LHLARKLLSEVRGQAHRFAESHLPGVNLYLLLPLGEQLPDVSLTFQAWRRL            99
6   51 LHLARKLLSEVRGQAHRFAESHLPGVNLYLLLPLGEQLPDVSLTFQAWRRL           100
       **************************************************

2  100 SDPERLCFISTTLQPFHAPLGGLGTQGRWTNMERMQLWAMRLDLRDLQRH           149
6  101 SDPERLCFISTTLQPFHAPLGGLGTQGRWTNMERMQLWAMRLDLRDLQRH           150
       **************************************************

2  150 LRFQVLAAGENLPEEEEEEEEEERKGLLPGALGSALQGPAQVSWPQL              199
6  151 LRFQVLAAGENLPEEEEEEEEEERKGLLPGALGSALQGPAQVSWPQL              200
       ***********************************************

2  200 LSTYRLLHSLELVLSRAVRELLLLSKAGHSVWPLGFPTLSPQP                  242
6  201 LSTYRLLHSLELVLSRAVRELLLLSKAGHSVWPLGFPTLSPQP                  243
       ******************************************
```

FIG. 1

```
  1  MGQTAGDLGWRLSLLLLPLLLVQAGSWGFPTDPLSLQELRREFTVSLYLA    50
  1                GLSLLLLPLLLVQAGSWGFPTDPLSLQELRREFTVSLYLA    40
                   *****************************

51  RKLLSEVQGYVHSFAESRLPGVNLDLLPLGYHLPNVSLTFQAWHHLSDSE   100
 41  RKLLSEVQGYVHSFAESRLPGVNLDLLPLGYHLPNVSLTFQAWHHLSDSE    90
     **************************************************

101  RLCFLATTLRPFPAMLGGLGTQGTWTSSEREQLWAMRLDLRDLHRHLRFQ   150
 91  RLCFLATTLRPFLAMLGGLGTQGTWTNIKRMQQWRLSLVLDVALCVFRSQ   140
     ************ ************ *   **** *** **.* *  **

151  VLAAGFKCSKEEEDKEEEEEEEEEEEKKLPLGALGGPNQVSSQVSWPQLLY   200
141  VLAAGFKCSKEEEDKEEEEEEEEEEEKKLPLGRLGGPNQVSSQVSWPQLLY   190
     ******************************* *****************

201  TYQLLHSLELVLSRAVRDLLLLSLPRRPGSAWDS      234
191  TYQLLHSMELVLSRAVRDLLLLSLPRRPGSALEFLTPSFKP   231
     *******.*********************.
```

FIG. 2

```
human IL-D80  001 MGQTAGDLGWRLSLLLLPLLLVQAGVWGFPRPPGRPQISLQELRREFTVSLHLARKLLSEVRGQAHRFAESHLPGVNLYL 080
              +++++++++++++++++++++++++++  ++++  +  +++++++++++++  ++++ +  + +++++++  +
mouse IL-D80  001 MGQTAGDLGWRLSLLLLPLLLVQAGSWGFPTDP.....LSLQELRREFTVSLYLARKLLSEVQGYVHSFAESRLPGVNLDL 076
```

Helix A

```
human IL-D80  081 LPLGEQLPDVSLTFQAWRRLSDPERLCFISTTLQPFHAPLGGLGTQGRWTNMERMQLWAMRLDLRDLQRHLRFQVLAAGF 160
                  +++ + ++ +++  +++++ +    ++  ++ +++ + ++++++++  ++ ++  + ++++++++++ +++++++++++
mouse IL-D80  077 LPLGYHLPNVSLTFQAWHHLSDSERLCFLATTLRPFFPAMIGGLGTQGTWTSSEREQLWAMRLDLRDLHRHLRFQVLAAGF 156
```

Helix B                                                              Helix C

```
human IL-D80  161 NLP...EEEEEEEEEEEEEEEERKGLLPGALGSALQGPAQVSWPQLLSTYRLLHSLELVLSRAVRELLLSKAGHSVWPLGFPTLSPQP 243
                   +        +++++++++++++++  +  + +                +++++ +++++++++ ++++++  + +++++
mouse IL-D80  157 KCSKEEEDKEEEEEEEEEKK.LPLGALGGPNQVSSQVSWPQLLYTYQLLHSLELVLHSRAVRDLLLSLPRRPGSAWDS 234
```

Helix D

MAMMALIAN CYTOKINES; RELATED REAGENTS

This filing is a divisional of U.S. patent application Ser. No. 10/000,776, filed Nov. 30, 2001, now issued as U.S. Pat. No. 7,148,300, which is a continuation-in-part of U.S. patent application Ser. No. 09/791,497, filed Feb. 22, 2001, now abandoned which is a continuation-in-part of U.S. patent application Ser. No. 09/627,897, filed Jul. 27, 2000, now abandoned and claims benefit from U.S. Provisional Patent Application Nos. 60/146,581, filed Jul. 30, 1999, and 60/147,763, filed Aug. 6, 1999, each of which are incorporated herein by reference in their entirety.

FIELD OF THE INVENTION

The present invention pertains to compositions related to proteins which function in controlling biology and physiology of mammalian cells, e.g., cells of a mammalian immune system. In particular, it provides purified genes, proteins, antibodies, and related reagents useful, e.g., to regulate activation, development, differentiation, and function of various cell types, including hematopoietic cells.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders. Some of these factors are hematopoietic growth and/or differentiation factors, e.g., stem cell factor (SCF) or IL-12. See, e.g., Mire-Sluis and Thorpe (1998) *Cytokines* Academic Press, San Diego; Thomson (ed. 1998) *The Cytokine Handbook* (3d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell.

Lymphokines apparently mediate cellular activities in a variety of ways. They have been shown to support the proliferation, growth, and differentiation of pluripotential hematopoietic stem cells into vast numbers of progenitors comprising diverse cellular lineages making up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

IL-12 plays a critical role in cell-mediated immunity (Gately et al. (1998) *Annu. Rev. Immunol,* 16:495-521; Trinchieri (1998) *Adv. Immunol;* 70:83-243; and Trinchieri (1995) *Annu. Rev. Immunol.* 13:251-276). Its activities are triggered through a high-affinity receptor complex that gathers two closely related subunits, IL-12R$\beta$1 and $\beta$2 (Chua, et al. (1995) *J. Immunol.* 155:4296-4294; and Preskey et al. (1996b) *Proc. Natl. Acad. sci. USA* 93:14002-14007). The p35 subunit has been suggested to bind to a second soluble cytokine receptor called EBI3 (Devergne et al. (1997) *Proc. Natl. Acad. Sci. USA* 94:12041-12046). As yet no biological activity has been reported for the p35-EBI3 pair, however, pairings of IL-12 subunits or IL-12-like subunits with other cytokines may provide information about cell-mediated immunity, e.g. T-cell regulation. Furthermore, the discovery of receptors or receptor subunits for these heteromeric cytokines will also provide information regarding immune regulation.

Research to better understand and treat various immune disorders has been hampered by the general inability to maintain cells of the immune system in vitro. Immunologists have discovered that culturing these cells can be accomplished through the use of T-cell and other cell supernatants, which contain various growth factors, including many of the lymphokines.

From the foregoing, it is evident that the discovery and development of new lymphokines and their related receptors or receptor subunits, e.g., related to the IL-6/IL-12 cytokine family could contribute to new therapies for a wide range of degenerative or abnormal conditions, which directly or indirectly involve the immune system and/or hematopoietic cells. In particular, the discovery and development of lymphokines which enhance or potentiate the beneficial activities of known lymphokines would be highly advantageous. The present invention provides new interleukin compositions, receptor subunits, and related compounds, and methods for their use.

BRIEF DESCRIPTION OF THE DRAWINGS

FIG. 1 shows the comparison between SEQ ID NO: 2 and the IL-D80 variant polypeptide of SEQ ID NO: 6.

FIG. 2 shows a comparison of rodent IL-D80 (SEQ ID NO: 4) and variant rodent IL-D80 (SEQ ID NO: 8) polypeptide sequences.

FIG. 3 shows a comparison of human IL-D80 (SEQ ID NO: 6) and rodent, e.g., mouse IL-D80 (SEQ ID NO: 8)

SUMMARY OF THE INVENTION

The present invention is directed to mammalian, e.g., rodent, canine, feline, primate, interleukin numbered DNAX 80 (IL-D80; p28) and its biological activities. The present invention is also based upon the discovery of the association of IL-D80 with the IL-12p40-like molecule, EBI3, and the binding of this composite cytokine to an IL-12Rβ2 subunit homologue known as WSX-1/TCCR. The IL-D80/EBI3 composite cytokine is also known as IL-27. It includes nucleic acids coding for polypeptides themselves and methods for their production and use. The nucleic acids of the invention are characterized, in part, by their homology to complementary DNA (cDNA) sequences disclosed herein, and/or by functional assays for growth factor- or cytokine-like activities, e.g., IL-6/IL-12 family of cytokines (see Thomson (1998) The Cytokine Handbook 3d ed., Academic Press, San Diego), applied to the polypeptides, which are typically encoded by these nucleic acids. Methods for modulating or intervening in the control of a growth factor dependent physiology or an immune response are provided.

The present invention is based, in part, upon the discovery of new cytokine sequences exhibiting significant sequence and structural similarity to the IL-6/IL12 family of cytokines. In particular, it provides primate, e.g., human, and rodent, e.g., mouse, sequences. Functional equivalents exhibiting significant sequence homology will be available from other mammalian, e.g., cow, horse, and rat, mouse, and non-mammalian species.

In various protein embodiments, the invention provides: a substantially pure or recombinant IL-D80 polypeptide exhibiting identity over a length of at least about 12 amino acids to SEQ ID NO: 2, 4, 6, or 8; a natural sequence IL-D80 of SEQ ID NO: 2, 4, 6, or 8; and a fusion protein comprising IL-D80 sequence of SEQ ID NO: 2, 4, 6, or 8. In certain embodiments, the segment of identity is at least about 14, 17, or 19 amino acids.

In other embodiments, the IL-D80 comprises a mature sequence comprising the sequences from SEQ ID NO:2, 4, 6, or 8; or exhibits a post-translational modification pattern distinct from natural IL-D80; or the polypeptide: is from a warm blooded animal selected from a mammal, including a primate; comprises at least one polypeptide segment of SEQ ID NO: 2, 4, 6, or 8; exhibits a plurality of amino acid residue fragments; is a natural allelic variant of IL-D80; has a length at least about 30 amino acids; exhibits at least two non-overlapping epitopes which are specific for a primate IL-D80; exhibits sequence identity over a length of at least about 20 amino acids to primate IL-D80; is glycosylated; has a molecular weight of at least 10 kD with natural glycosylation; is a synthetic polypeptide; is attached to a solid substrate; is conjugated to another chemical moiety; is a 5-fold or less substitution from natural sequence; or is a deletion or insertion variant from a natural sequence. Preferred embodiments include a composition comprising: a sterile IL-D80 polypeptide; or the IL-D80 polypeptide and a carrier, wherein the carrier is: an aqueous compound, including water, saline, and/or buffer; and/or formulated for oral, rectal, nasal, topical, or parenteral administration. In fusion protein embodiments, the protein can have: mature polypeptide sequence from SEQ ID NO:2, 4, 6, or 8; a detection or purification tag, including a FLAG, His6, or Ig sequence; and/or sequence of another cytokine or chemokine, including an IL-12.

Kit embodiments include those with an IL-D80 polypeptide, and: a compartment comprising the polypeptide; and/or instructions for use or disposal of reagents in the kit.

In binding compound embodiments, the compound may have an antigen binding site from an antibody, which specifically binds to a natural IL-D80 polypeptide, wherein: the IL-D80 is a primate protein; the binding compound is an Fv, Fab, or Fab2 fragment; the binding compound is conjugated to another chemical moiety; or the antibody: is raised against a peptide sequence of a mature polypeptide portion from SEQ ID NO:2, 4, 6, or 8; is raised against a mature IL-D80; is raised to a purified primate IL-D80; is immunoselected; is a polyclonal antibody; binds to a denatured IL-D80; exhibits a Kd of at least 30 µM; is attached to a solid substrate, including a bead or plastic membrane; is in a sterile composition; or is detectably labeled, including a radioactive or fluorescent label. Kits containing binding compounds include those with: a compartment comprising the binding compound; and/or instructions for use or disposal of reagents in the kit. Often the kit is capable of making a qualitative or quantitative analysis. Preferred compositions will comprise: a sterile binding compound; or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding an IL-D80 polypeptide or fusion protein, wherein: the IL-D80 is from a primate; and/or the nucleic acid: encodes an antigenic peptide sequence of SEQ ID NO:2, 4, 6, or 8; encodes a plurality of antigenic peptide sequences of SEQ ID NO:2, 4, 6, or 8; exhibits identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a primate, including a human; comprises a natural full length coding sequence; is a hybridization probe for a gene encoding the IL-D80; or is a PCR primer, PCR product, or mutagenesis primer. The invention also provides a cell, tissue, or organ comprising such a recombinant nucleic acid, and preferably the cell will be: a prokaryotic cell; a eukaryotic cell; a bacterial cell; a yeast cell; an insect cell; a mammalian cell; a mouse cell; a primate cell; or a human cell.

Kit embodiments include those with such nucleic acids, and: a compartment comprising the nucleic acid; a compartment further comprising the IL-D80 protein or polypeptide; and/or instructions for use or disposal of reagents in the kit. Typically, the kit is capable of making a qualitative or quantitative analysis.

In certain embodiments, the nucleic acid: hybridizes under wash conditions of 30° C. and less than 2M salt, or of 45° C. and/or 500 mM salt, or 55° C. and/or 150 mM salt, to SEQ ID NO: 1, 3, 5, or 7; or exhibits identity over a stretch of at least about 30, 55, or 75 nucleotides, to a primate IL-D80.

The invention embraces a method of modulating physiology or development of a cell or tissue culture cells comprising contacting the cell with an agonist or antagonist of a primate IL-D80. The method may be where: the contacting is in combination with an agonist or antagonist of IL-12; or the contacting is with an antagonist, including a binding composition comprising an antibody binding site which specifically binds an IL-D80.

The invention further provides a composite cytokine (IL-27) comprising a plurality of segments of SEQ ID NO:2, 4, 6, or 8 and SEQ ID NO:10. Also encompassed is an isolated or recombinant polynucleotide encoding the composite cytokine of said composite cytokine. Further provided is a receptor subunit:ligand composition comprising a plurality of polypeptide segments of SEQ ID NO:2, 4, 6, or 8, SEQ ID NO:10, and SEQ ID NO:12.

DETAILED DESCRIPTION OF THE PREFERRED EMBODIMENTS

All references cited herein are incorporated herein by reference to the same extent as if each individual publication or patent application was specifically and individually indicated to be incorporated by reference.

I. General

The present invention provides amino acid sequences and DNA sequences encoding various mammalian proteins, which are cytokines, e.g., which are secreted molecules which can mediate a signal between immune or other cells. See, e.g., Paul (1997) *Fundamental Immunology* (3d ed.) Raven Press, N.Y. The full length cytokines, and fragments, or antagonists will be useful in physiological modulation of cells expressing a receptor. It is likely that IL-D80 or IL-27 has either stimulatory or inhibitory effects on hematopoietic cells, including, e.g., lymphoid cells, such as T-cells, B-cells, natural killer (NK) cells, macrophages, dendritic cells, hematopoietic progenitors, etc. In particular, the IL-27 composite cytokine may play a role in inflammation, including, but not limited to ulcerative colitis, arthritis, etc. The proteins will also be useful as antigens, e.g., immunogens, for raising antibodies to various epitopes on the protein, both linear and conformational epitopes.

A cDNA encoding IL-D80 was identified from various primate, e.g., human, sequences of BACs of Chromosome 16. See, e.g., CIT987SK-A-575C2, and CIT987SK-A-761H5. The molecule was designated huIL-D80. A human EST has been identified and described, human EST AI085007. A mouse EST AA266872 has also been identified and described.

The primate, e.g., human, gene will encode a small soluble cytokine-like protein of about 243 amino acids. See SEQ. ID. NOs: 1, 2, 5, and 6. Exon boundaries are likely to correspond to about 219/220; 393/394; 492/493; and 551/552 of SEQ ID NO:1. Coding segments corresponding to those boundaries are particularly interesting. Translated amino acid sequence, which is encoded by nucleotides 193 to 918 of SEQ ID NO:1, is shown in SEQ ID NO: 2.

A predicted signal cleavage site may exist between about residues 25-30 of SEQ ID NO: 2; helix A is predicted to run from about residues 33-38 to about residues 54-59 of SEQ ID NO: 2; helix B is predicted to run from about residues 85-90 to about residues 111-116 of SEQ ID NO: 2; helix C is predicted to run from about residues 121-126 to about residues 154-159 of SEQ ID NO: 2; and helix D is predicted to run from about residues 201-206 to about residues 228-233 of SEQ ID NO: 2.

SEQ ID NO: 5 shows a variant of IL-D80 and SEQ ID NO: 6 is the encoded polypeptide. FIG. 1 shows the comparison between SEQ ID NO: 2 and the IL-D80 variant polypeptide of SEQ ID NO: 6. Structural motifs are as indicated above with the appropriate change in residue positions.

The corresponding rodent polynucleotide sequence of IL-D80 is shown in SEQ ID NO: 3. Exon boundaries are likely to run from about 198/199; 360/361; 459/460; and 618/619. The predicted polypeptide sequence, which runs from about nucleotide 199 to 891 of SEQ ID NO: 3, is shown in SEQ ID NO: 4. The predicted signal cleavage site runs from about residue 16-21 of SEQ ID NO: 4; helix A is predicted to run from about residue 21-26 to about residue 41-46; helix B is predicted to run from about residue 72-77 to about residue 101-106; helix C is predicted to run from about residue 108-133 to about residue 141-146; and helix D is predicted to run from about residue 185-190 to about residue 211-215. All postions refer to SEQ ID NO: 4. A variant rodent IL-D80 polynucleotide sequence is shown in SEQ ID NO: 7 and the predicted polypeptide sequence is shown in SEQ ID NO: 8. A comparison of rodent IL-D80 (SEQ ID NO: 4) and variant rodent IL-D80 (SEQ ID NO: 8) polypeptide sequences is shown in FIG. 2.

IL-D80 exhibits structural motifs characteristic of a member of the long chain cytokines belonging to the IL-6/IL-12 family of cytokines. The structural homology of IL-D80 to related cytokine proteins suggests related function of this molecule.

The IL-D80 cDNA sequences mature proteins with calculated molecular mass of 24.5 and 23.6 kDa. No N-glycosylation sites are found in hIL-D80, but several O-glycosylation sites are predicted. Murine IL-D80 contains one potential N-glycosylation site (N85). Transient expression of mp28 in the presence or absence of tunicamycin indicated that mp28 is indeed N-linked glycosylated. Both human and mouse IL-D80 display an unusual sequence insertion in the predicted loop region between helix C and D. In hIL-D80, the C-D loop contains a stretch of 13 glutamic acid residues; mp28 displays 14 negatively charged residues in this region, interrupted by one lysine residue. This highly charged sequence has not been observed in any other helical cytokine and most likely will affect the biophysical properties of the protein in solution. Overall, human and mouse IL-D80 are 74% identical.

Comparison of the sequences will also provide an evolutionary tree. This can be generated, e.g., using the TreeView program in combination with the ClustalX analysis software program. See Thompson, et al. *Nuc. Acids Res.* 25:4876-4882; and TreeView, Page, IBLS, University of Glasgow, e-mail rpage@bio.gla.ac.uk; http://taxonomy.zoology.gla.ac.uk.rod.treeview.html.

Co-transfection of human Epstein-Barr virus-induced gene 3 (EBI3; GenBank NM005755; Devergne, et al. (1996) *J. Virol.* 70:1143-1153; SEQ ID NOs: 9 and 10) cDNA and human IL-D80 cDNA leads to enhanced secretion of IL-D80. IL-D80 co-immunoprecipitated with EBI3, and conversely, EBI3 co-immunoprecipitated with IL-D80. This indicates that these two proteins form a composite factor that either itself has biological functions (that neither protein has on its own) or EBI3 is used as a shuttle to release IL-D80 in the supernatant. Of note, EBI3 is also expressed in vivo by activated antigen presenting cells (APCs) and at very high levels by placental syncytiotrophoblasts. The present invention provides the first evidence that the IL-80D/EBI3 composite cytokine (IL-27) binds to an IL-12R-like subunit, WSX-1/TCCR (See, e.g., GenBank AF265242; Chen, et al. (2000) *Nature* 407:916-920; SEQ ID NO: 11 and 12).

Biologically, IL-27 is produced by antigen presenting cells (APCs). In contrast to other similar heterodimers made by APCs, i.e., IL-12 (p35+p40) and IL-23 (p19+p40), kinetic analysis of IL-27 showed that this composite cytokine is produced earlier in activation of APCs. Thus, IL-27 can be a potent adjuvant of a Th1 response.

The primary activity of IL-27 triggers rapid clonal expansion of antigen specific for naive human and mouse CD4+ T cells. Moreover, it promotes Th1 polarization and IFN-γ production of naïve CD4+ T cells. Mechanistically, these naïve T cells are primed to respond to IL-27 by the production of this composite cytokine by the APCs which interact with these cells. These activities of IL-27 are dependent on simultaneous T cell receptor activation and occur in synergy with IL-12.

IL-D80 or IL-27 agonists, or antagonists, may also act as functional or receptor antagonists. Thus, IL-D80, IL-27, WSX-1/TCCR, or its antagonists, may be useful in the treatment of abnormal medical conditions, including immune disorders, e.g., T cell immune deficiencies, inflammation, or tissue rejection, or in cardiovascular or neurophysiological conditions.

The natural antigens are capable of mediating various biochemical responses which lead to biological or physiological responses in target cells. The preferred embodiment characterized herein is from human, but other primate, or other species counterparts exist in nature. Additional sequences for proteins in other mammalian species, e.g., primates, canines, felines, and rodents, should also be available, particularly the domestic animal species. See below. The descriptions below are directed, for exemplary purposes, to a human IL-D80 or IL-27, but are likewise applicable to related embodiments from other species.

II. Purified IL-D80 or IL-27

Mammlian IL-D80 amino acid sequence, is shown in several embodiments, e.g., SEQ ID NO: 2, 4, 6, or 8. EBI3 amino acid sequence is provided in SEQ ID NO: 10. Other naturally occurring nucleic acids which encode the protein can be isolated by standard procedures using the provided sequence, e.g., PCR techniques, or by hybridization. These amino acid sequences, provided amino to carboxy, are important in providing sequence information for the cytokine allowing for distinguishing the protein antigen from other proteins and exemplifying numerous variants. Moreover, the peptide sequences allow preparation of peptides to generate antibodies to recognize such segments, and nucleotide sequences allow preparation of oligonucleotide probes, both of which are strategies for detection or isolation, e.g., cloning, of genes encoding such sequences.

As used herein, the term "human soluble IL-D80 or IL-27" shall encompass, when used in a protein context, a protein having amino acid sequence corresponding to a soluble polypeptide shown in SEQ ID NO: 2 or 6, or significant fragments thereof. Preferred embodiments comprise a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

Binding components, e.g., antibodies, typically bind to an IL-D80 or IL-27 with high affinity, e.g., at least about 100 nM, usually better than about 30 nM, preferably better than about 10 nM, and more preferably at better than about 3 nM. Counterpart proteins will be found in mammalian species other than human, e.g., other primates, ungulates, or rodents. Non-mammalian species should also possess structurally or functionally related genes and proteins, e.g., birds or amphibians.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, 60, 75, 100, etc. Such fragments may have ends which begin and/or end at virtually all positions, beginning at residues 1, 2, 3, etc., and ending at, e.g., 150, 149, 148, etc., in all practical combinations. Particularly interesting peptides have ends corresponding to structural domain boundaries, e.g., helices A, B, C, and/or D.

The term "binding composition" refers to molecules that bind with specificity to IL-D80 or IL-27, e.g., in an antibody-antigen interaction. The specificity may be more or less inclusive, e.g., specific to a particular embodiment, or to groups of related embodiments, e.g., primate, rodent, etc. It also includes compounds, e.g., proteins, which specifically associate with IL-D80 or IL-27, including in a natural physiologically relevant protein-protein interaction, either covalent or non-covalent. The molecule may be a polymer, or chemical reagent. A functional analog may be a protein with structural modifications, or it may be a molecule which has a molecular shape which interacts with the appropriate binding determinants. The compounds may serve as agonists or antagonists of a receptor binding interaction, see, e.g., Goodman, et al. (eds.) *Goodman & Gilman's: The Pharmacological Bases of Therapeutics* (current ed.) Pergamon Press.

Substantially pure, e.g., in a protein context, typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein. In other instances, a harsh detergent may be used to effect significant denaturation.

The above will also be applicable to the IL-D80 or IL-27/EBI3 composite cytokine, where SEQ ID NO: 10 is the polypeptide sequence of EBI3.

III. Physical Variants

This invention also encompasses proteins or peptides having substantial amino acid sequence identity with the amino acid sequence of the IL-D80 or IL-27 antigen. The variants include species, polymorphic, or allelic variants.

Amino acid sequence homology, or sequence identity, is determined by optimizing residue matches, if necessary, by introducing gaps as required. See also Needleham, et al. (1970) *J. Mol. Biol.* 48:443-453; Sankoff, et al. (1983) Chapter One in *Time Warps, String Edits, and Macromolecules: The Theory and Practice of Sequence Comparison*, Addison-Wesley, Reading, Mass.; and software packages from Intelli-Genetics, Mountain View, Calif.; and the University of Wisconsin Genetics Computer Group, Madison, Wis. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. The conservation may apply to biological features, functional features, or structural features. Homologous amino acid sequences are typically intended to include natural polymorphic or allelic and interspecies variations of a protein sequence. Typical homologous proteins or peptides will have from 25-100% identity (if gaps can be introduced), to 50-100% identity (if conservative substitutions are included) with the amino acid sequence of the IL-D80 or IL-27. Identity measures will be at least about 35%, generally at least about 40%, often at least about 50%, typically at least about 60%, usually at least about 70%, preferably at least about 80%, and more preferably at least about 90%.

The isolated IL-D80 or IL-27 DNA can be readily modified by nucleotide substitutions, nucleotide deletions, nucleotide insertions, and inversions of short nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant IL-D80 or IL-27" encompasses a polypeptide otherwise falling within the sequence identity definition of the IL-D80 or IL-27 as set forth above, but having an amino acid sequence which differs from that of IL-D80 or IL-27 as normally found in nature, whether by way of deletion, substitution, or insertion. This generally includes proteins having significant identity with a protein having sequence of SEQ ID NO: 2, 4, 6, or 8, or the foregoing in association with SEQ ID NO: 10 and as sharing various biological activities, e.g., antigenic or immunogenic, with those sequences, and in preferred embodiments contain most of the natural full length disclosed sequences. Full length sequences will typically be preferred, though truncated versions will also be useful, likewise, genes or proteins found from natural sources are typically most desired. Similar concepts apply to different IL-D80 or IL-27 proteins, particularly those found in various warm blooded animals, e.g., mammals and birds. These descriptions are generally meant to encompass many IL-D80 or IL-27 proteins, not limited to the particular mammalian embodiments specifically discussed.

IL-D80 or IL-27 mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Methods in Enzymol.* 154:367-382. Preferred embodiments include, e.g., 1-fold, 2-fold, 3-fold, 5-fold, 7-fold, etc., preferably conservative substitutions at the nucleotide or amino acid levels. Preferably the substitutions will be away from the conserved cysteines, and often will be in the regions away from the helical structural domains. Such variants may be useful to produce specific antibodies, and often will share many or all biological properties.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, target-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

Structural analysis can be applied to this gene, in comparison to the IL-12 family of cytokines. In particular, $\beta$-sheet and $\alpha$-helix residues can be determined using, e.g., RASMOL program, see Bazan, et al. (1996) *Nature* 379:591; Lodi, et al. (1994) *Science* 263:1762-1766; Sayle and Milner-White (1995) *Trends in Biol. Sci.* 20:374-376; and Gronenberg, et al. (1991) *Protein Engineering* 4:263-269. Preferred residues for substitutions include the surface exposed residues which would be predicted to interact with receptor. Other residues which should conserve function will be conservative substitutions, particularly at positions far from the surface exposed residues.

The above will also be applicable for the IL-D80 or IL-27 (i.e., IL-D80+EBI3) composite cytokine where SEQ ID NO: 10 is the polypeptide sequence of EBI3.

IV. Functional Variants

The blocking of physiological response to IL-D80 or the IL-27 composite cytokine may result from the competitive inhibition of binding of the ligand to its receptor.

In vitro assays of the present invention will often use isolated protein, soluble fragments comprising receptor binding segments of these proteins, or fragments attached to solid phase substrates. These assays will also allow for the diagnostic determination of the effects of either binding segment mutations and modifications, or cytokine mutations and modifications, e.g., IL-D80 or IL-27 analogs.

This invention also contemplates the use of competitive drug screening assays, e.g., where neutralizing antibodies to the cytokine, or receptor binding fragments compete with a test compound.

"Derivatives" of IL-D80 or IL-27 antigens include amino acid sequence mutants from naturally occurring forms, glycosylation variants, and covalent or aggregate conjugates with other chemical moieties, e.g., PEGylation. Covalent derivatives can be prepared by linkage of functionalities to groups which are found in IL-D80 or IL-27 amino acid side chains or at the N- or C-termini, e.g., by standard means. See, e.g., Lundblad and Noyes (1988) *Chemical Reagents for Protein Modification*, vols. 1-2, CRC Press, Inc., Boca Raton, Fla.; Hugli (ed. 1989) *Techniques in Protein Chemistry*, Academic Press, San Diego, Calif.; and Wong (1991) *Chemistry of Protein Conjugation and Cross Linking*, CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497-534. Also embraced are versions of the peptides with the same primary amino acid sequence which have other minor modifications, including phosphorylated amino acid residues, e.g., phosphotyrosine, phosphoserine, or phosphothreonine.

Fusion polypeptides between IL-D80 or IL-27 and other homologous or heterologous proteins are also provided. Many cytokine receptors or other surface proteins are multimeric, e.g., homodimeric entities, and a repeat construct may have various advantages, including lessened susceptibility to proteolytic cleavage. Typical examples are fusions of a reporter polypeptide, e.g., luciferase, with a segment or domain of a protein, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, yeast alpha mating factor, and detection or purification tags such as a FLAG sequence of His6 sequence. See, e.g., Godowski, et al. (1988) *Science* 241:812-816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1-3, Cold Spring Harbor Laboratory; and Ausubel, et al. (eds. 1993) *Current Protocols in Molecular Biology*, Greene and Wiley, NY. Techniques for synthesis of polypeptides are described, e.g., in Merrifield (1963) *J. Amer. Chem. Soc.* 85:2149-2156; Merrifield (1986) *Science* 232: 341-347; Atherton, et al. (1989) *Solid Phase Peptide Synthesis: A Practical Approach*, IRL Press, Oxford; and Grant (1992) *Synthetic Peptides: A User's Guide*, W. H. Freeman, NY. Refolding methods may be applicable to synthetic proteins.

This invention also contemplates the use of derivatives of IL-D80 or IL-27 proteins other than variations in amino acid sequence or glycosylation. Such derivatives may involve covalent or aggregative association with chemical moieties or protein carriers. Covalent or aggregative derivatives will be useful as immunogens, as reagents in immunoassays, or in purification methods such as for affinity purification of binding partners, e.g., other antigens. An IL-D80 or IL-27 can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-IL-D80 or IL-27 antibodies or an alternative binding composition. The IL-D80 or IL-27 proteins can also be labeled with a detectable group, e.g., for use in diagnostic assays. Purification of IL-D80 or IL-27 may be effected by an immobilized antibody or complementary binding partner, e.g., binding portion of a receptor.

A solubilized IL-D80 or IL-27, or fragments of this invention can be used as an immunogen for the production of antisera or antibodies specific for binding. Purified antigen can be used to screen monoclonal antibodies or antigen-binding fragments, encompassing antigen binding fragments of natural antibodies, e.g., Fab, Fab', F(ab)$_2$, etc. Purified IL-D80 or IL-27 antigens can also be used as a reagent to detect antibodies generated in response to the presence of elevated levels of the cytokine, which may be diagnostic of an abnormal or specific physiological or disease condition. This invention contemplates antibodies raised against amino acid sequences encoded by nucleotide sequence shown in SEQ ID NO: 1, 3, 5, or 7, or fragments of proteins containing it. Also contemplated are sequences encoding the IL-D80 or IL-27 cytokines, or fragments thereof. In particular, this invention contemplates antibodies having binding affinity to or being raised against specific domains, e.g., helices A, B, C, or D.

The present invention contemplates the isolation of additional closely related species variants. Southern and Northern blot analysis will establish that similar genetic entities exist in other mammals. It is likely that IL-D80 or IL-27s are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the molecules will be greatly accelerated by the isolation and characterization of additional distinct species or polymorphic variants of them. In particular, the present invention provides useful probes for identifying additional homologous genetic entities in different species.

The isolated genes will allow transformation of cells lacking expression of an IL-D80 or IL-27, e.g., either species types or cells which lack corresponding proteins and exhibit negative background activity. This should allow analysis of the function of IL-D80 or IL-27 in comparison to untransformed control cells.

Dissection of critical structural elements which effect the various physiological functions mediated through these antigens is possible using standard techniques of modern molecular biology, particularly in comparing members of the related class. See, e.g., the homolog-scanning mutagenesis technique described in Cunningham, et al. (1989) *Science* 243:1339-1336; and approaches used in O'Dowd, et al. (1988) *J. Biol. Chem.* 263:15985-15992; and Lechleiter, et al. (1990) *EMBO J.* 9:4381-4390.

Intracellular functions would probably involve receptor signaling. However, protein internalization may occur under certain circumstances, and interaction between intracellular components and cytokine may occur. Specific segments of interaction of IL-D80 or IL-27 with interacting components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of IL-D80 or IL-27 will be pursued. The controlling elements associated with the antigens should exhibit differential physiological, developmental, tissue specific, or other expression patterns. Upstream or downstream genetic regions, e.g., control elements, are of interest.

Structural studies of the IL-D80 or IL-27 antigens will lead to design of new antigens, particularly analogs exhibiting agonist or antagonist properties on the molecule. This can be combined with previously described screening methods to isolate antigens exhibiting desired spectra of activities.

V. Antibodies

Antibodies can be raised to various epitopes of the IL-D80 or IL-27 proteins, including species, polymorphic, or allelic variants, and fragments thereof, both in their naturally occurring forms and in their recombinant forms. Additionally, antibodies can be raised to IL-D80 or IL-27 s in either their active forms or in their inactive forms, including native or denatured versions. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective IL-D80 or IL-27s, or screened for agonistic or antagonistic activity, e.g., mediated through a receptor. Antibodies may be agonistic or antagonistic, e.g., by sterically blocking binding to a receptor. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

An IL-D80 or IL-27 protein that specifically binds to or that is specifically immunoreactive with an antibody generated against a defined immunogen, such as an immunogen consisting of the amino acid sequence of SEQ ID NO: 2, 4, 6, or 8, or any of the foregoing in association with SEQ ID NO: 10, is typically determined in an immunoassay. The immunoassay typically uses a polyclonal antiserum which was raised, e.g., to a polypeptide of SEQ ID NO: 2, 4, 6, or 8, or any of the foregoing in association with SEQ ID NO: 10. This antiserum is selected to have low crossreactivity against other IL12 family members, e.g., human or rodent IL-12, preferably from the same species, and any such crossreactivity is removed by immunoabsorption prior to use in the immunoassay.

In order to produce antisera for use in an immunoassay, the protein of SEQ ID NO: 2, 4, 6, or 8, or the foregoing in association with SEQ ID NO: 10, or a combination thereof, is isolated as described herein. For example, recombinant protein may be produced in a mammalian cell line. An appropriate host, e.g., an inbred strain of mice such as Balb/c, is immunized with the selected protein, typically using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-12 family members, e.g., rodent IL-12, using a competitive binding immunoassay such as the one described in Harlow and Lane, supra, at pages 570-573. Preferably at least one other IL-12 family member is used in this determination in conjunction with, e.g., the primate IL-12. The IL-12 family members can be produced as recombinant proteins and isolated using standard molecular biology and protein chemistry techniques as described herein.

Immunoassays in the competitive binding format can be used for the crossreactivity determinations. For example, the protein of SEQ ID NO: 2 or 6 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2 or 6. Similarly, the composite cytokine of SEQ ID NO: 2 or 6 in association with SEQ ID NO: 10 can be used. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the IL-12 like protein of SEQ ID NO: 2, 4, 6, or 8, or any of the foregoing in association with SEQ ID NO: 10). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying IL-D80 or IL-27 protein or its receptors, e.g., WSX-1/TCCR (SEQ ID NO: 12). See, e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y. Cross absorptions, depletions, or other means will provide preparations of defined selectivity, e.g., unique or shared species specificities. These may be the basis for tests which will identify various groups of antigens.

Further, the antibodies, including antigen binding fragments, of this invention can be potent antagonists that bind to the antigen and inhibit functional binding, e.g., to a receptor which may elicit a biological response. They also can be useful as non-neutralizing antibodies and can be coupled to toxins or radionuclides so that when the antibody binds to antigen, a cell expressing it, e.g., on its surface, is killed. Further, these antibodies can be conjugated to drugs or other therapeutic agents, either directly or indirectly by means of a linker, and may effect drug targeting.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, vol. 1, Academic Press, New York; and Harlow and Lane (1988) *Antibodies: A Laboratory Manual*, CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) *Nature* 256:495-497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029-10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3-55. The converse may be used to purify antibodies.

Antibodies raised against each IL-D80 or IL-27 will also be useful to raise anti-idiotypic antibodies. These will be useful in detecting or diagnosing various immunological conditions related to expression of the respective antigens.

VI. Nucleic Acids

The described peptide sequences and the related reagents are useful in detecting, isolating, or identifying a DNA clone encoding IL-D80 or IL-27, e.g., from a natural source. Typically, it will be useful in isolating a gene from mammal, and similar procedures will be applied to isolate genes from other species, e.g., warm blooded animals, such as birds and mammals. Cross hybridization will allow isolation of IL-D80 or IL-27 from the same, e.g., polymorphic variants, or other species. A number of different approaches will be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual*, Cold Spring Harbor Press.

For example, the specific binding composition could be used for screening of an expression library made from a cell line which expresses an IL-D80 or IL-27. Screening of intracellular expression can be performed by various staining or immunofluorescence procedures. Binding compositions could be used to affinity purify or sort out cells expressing a surface fusion protein.

The peptide segments can also be used to predict appropriate oligonucleotides to screen a library. The genetic code can be used to select appropriate oligonucleotides useful as probes for screening. See, e.g., SEQ ID NO: 1, 3, 5, or 7, or any of the foregoing in addition to SEQ ID NO: 9. In combination with polymerase chain reaction (PCR) techniques, synthetic oligonucleotides will be useful in selecting correct clones from a library. Complementary sequences will also be used as probes, primers, or antisense strands. Various fragments should be particularly useful, e.g., coupled with anchored vector or poly-A complementary PCR techniques or with complementary DNA of other peptides.

This invention contemplates use of isolated DNA or fragments to encode an antigenic or biologically active corresponding IL-D80 or IL-27 polypeptide, particularly lacking the portion coding the untranslated 5' portion of the described sequence. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence disclosed in, e.g., SEQ ID NO: 2, 4, 6, or 8, or any of the foregoing in association with SEQ ID NO: 10, particularly a mature, secreted polypeptide. Further, this invention covers the use of isolated or recombinant DNA, or fragments thereof, which encode proteins which exhibit high identity to a secreted IL-D80 or IL-27. The isolated DNA can have the respective regulatory sequences in the 5' and 3' flanks, e.g., promoters, enhancers, poly-A addition signals, and others. Alternatively, expression may be effected by operably linking a coding segment to a heterologous promoter, e.g., by inserting a promoter upstream from an endogenous gene.

An "isolated" nucleic acid is a nucleic acid, e.g., an RNA, DNA, or a mixed polymer, which is substantially separated from other components which naturally accompany a native sequence, e.g., ribosomes, polymerases, and/or flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, e.g., products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species or polymorphic variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides, e.g., 67, 73, 81, 89, 95, 150, 200, 250, 300, 500, etc.

A DNA which codes for an IL-D80 or IL-27 protein will be particularly useful to identify genes, mRNA, and cDNA species which code for related or similar proteins, as well as DNAs which code for homologous proteins from different species. There will be homologs in other species, including primates, rodents, canines, felines, birds, and fish. Various IL-D80 or IL-27 proteins should be homologous and are encompassed herein. However, even proteins that have a more distant evolutionary relationship to the antigen can readily be isolated under appropriate conditions using these sequences if they are sufficiently homologous. Primate IL-D80 or IL-27 proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology*, Academic Press, San Diego, pp. 1502-1504; Travis (1992) *Science* 256:1392-1394; Kuhn, et al. (1991) *Science* 254:707-710; Capecchi (1989) *Science* 244:1288; Robertson (ed. 1987) *Teratocarcinomas and Embryonic Stem Cells: A Practical Approach*, IRL Press, Oxford; Rosenberg (1992) *J. Clinical Oncology* 10:180-199; and Cournoyer and Caskey (1993) *Ann. Rev. Immunol.* 11:297-329. Alternatively, expression may be effected by operably linking a coding segment to a heterologous promoter, e.g., by inserting a promoter upstream from an endogenous gene. See, e.g., Treco, et al. WO96/29411 or U.S. Ser. No. 08/406,030.

Substantial homology, e.g., identity, in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of IL-D80 or IL-27, e.g., in SEQ ID NO: 1, 3, 5, or 7, or any of the foregoing in association with SEQ ID NO: 9. Typically, selective hybridization will occur when there is at least about 55% identity over a stretch of at least about 30 nucleotides, preferably at least about 75% over a stretch of about 25 nucleotides, and most preferably at least about 90% over about 20 nucleotides. See, Kanehisa (1984) *Nuc. Acids Res.* 12:203-213. The length of identity comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., 60° C., or 65° C., and preferably excess of about 70° C. Stringent salt conditions will ordinarily be less than about 1000 mM, usually less than about 400 mM, typically less than about 250 mM, preferably less than about 150 mM, including about 100, 50, or even 20 mM. However, the combination of parameters is much more important than the measure of any single parameter. See, e.g., Wetmur and Davidson (1968) *J. Mol. Biol.* 31:349-370. Hybridization under stringent conditions should give a background of at least 2-fold over background, preferably at least 3-5 or more.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403-410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

IL-D80 or IL-27 from other mammalian species can be cloned and isolated by cross-species hybridization of closely related species. Homology may be relatively low between distantly related species, and thus hybridization of relatively closely related species is advisable. Alternatively, preparation of an antibody preparation which exhibits less species specificity may be useful in expression cloning approaches.

VII. Making IL-D80 or IL-27; Mimetics

DNA which encodes the IL-D80 or IL-27 or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161-170; Gubler and Hoffman (1983) *Gene* 25:263-269; and Glover (ed. 1984) *DNA Cloning: A Practical Approach,* IRL Press, Oxford. Alternatively, the sequences provided herein provide useful PCR primers or allow synthetic or other preparation of suitable genes encoding an IL-D80 or IL-27; including naturally occurring embodiments.

This DNA can be expressed in a wide variety of host cells for the synthesis of a full-length IL-D80 or IL-27 or fragments which can in turn, e.g., be used to generate polyclonal or monoclonal antibodies; for binding studies; for construction and expression of modified molecules; and for structure/function studies. There may be a need for a chaparone protein for efficient secretion, or additional steps may be necessary to retrieve the protein from the intracellular compartment.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual,* Elsevier, N.Y.; and Rodriguez, et al. (eds. 1988) *Vectors: A Survey of Molecular Cloning Vectors and Their Uses,* Buttersworth, Boston, Mass.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See, e.g., Rodriguez, et al., Chapter 10, pp. 205-236; Balbas and Bolivar (1990) *Methods in Enzymology* 185:14-37; and Ausubel, et al. (1993) *Current Protocols in Molecular Biology,* Greene and Wiley, N.Y.

Representative examples of suitable expression vectors include pCDNA1; pCD, see Okayama, et al. (1985) *Mol. Cell Biol.* 5:1136-1142; pMC1neo Poly-A, see Thomas, et al. (1987) *Cell* 51:503-512; and a baculovirus vector such as pAC 373 or pAC 610. See, e.g., Miller (1988) *Ann. Rev. Microbiol.* 42:177-199.

It will often be desired to express an IL-D80 or IL-27 polypeptide in a system which provides a specific or defined glycosylation pattern. See, e.g., Luckow and Summers (1988) *Bio/Technology* 6:47-55; and Kaufman (1990) *Meth. Enzymol.* 185:487-511.

The IL-D80 or IL-27, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427-454; Tse, et al. (1985) *Science* 230:1003-1008; and Brunner, et al. (1991) *J. Cell Biol.* 114:1275-1283.

Now that the IL-D80 or IL-27 has been characterized, fragments or derivatives thereof can be prepared by conventional processes for synthesizing peptides. These include processes such as are described in Stewart and Young (1984)

*Solid Phase Peptide Synthesis*, Pierce Chemical Co., Rockford, Ill.; Bodanszky and Bodanszky (1984) *The Practice of Peptide Synthesis*, Springer-Verlag, New York; Bodanszky (1984) *The Principles of Peptide Synthesis*, Springer-Verlag, New York; and Villafranca (ed. 1991) *Techniques in Protein Chemistry II*, Academic Press, San Diego, Calif.

VIII. Uses

The present invention provides reagents which will find use in diagnostic applications as described elsewhere herein, e.g., in IL-D80 or IL-27 mediated conditions, or below in the description of kits for diagnosis. The gene may be useful in forensic sciences, e.g., to distinguish rodent from human, or as a marker to distinguish between different cells exhibiting differential expression or modification patterns.

This invention also provides reagents with significant commercial and/or therapeutic potential. The IL-D80 or IL-27 (naturally occurring or recombinant), fragments thereof, and antibodies thereto, along with compounds identified as having binding affinity to IL-D80 or IL-27, should be useful as reagents for teaching techniques of molecular biology, immunology, or physiology. Appropriate kits may be prepared with the reagents, e.g., in practical laboratory exercises in production or use of proteins, antibodies, cloning methods, histology, etc.

The reagents will also be useful in the treatment of conditions associated with abnormal physiology or development, including inflammatory conditions. They may be useful in vitro tests for presence or absence of interacting components, which may correlate with success of particular treatment strategies. In particular, modulation of physiology of various, e.g., hematopoietic or lymphoid, cells will be achieved by appropriate methods for treatment using the compositions provided herein. See, e.g., Thomson (ed. 1998) *The Cytokine Handbook* (3d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

For example, a disease or disorder associated with abnormal expression or abnormal signaling by an IL-D80 or IL-27 should be a likely target for an agonist or antagonist. Similarly, the binding partner of the IL-27 composite cytokine, WSX-1/TCCR, should also be a target. The new cytokine should play a role in regulation or development of hematopoietic cells, e.g., lymphoid cells, which affect immunological responses, e.g., inflammation and/or autoimmune disorders. Alternatively, it may affect vascular physiology or development, or neuronal effects.

In particular, the cytokine should mediate, in various contexts, cytokine synthesis by the cells, proliferation, etc. Antagonists of IL-D80 or IL-27, such as mutein variants of a naturally occurring form of IL-D80 or IL-27 or blocking antibodies, may provide a selective and powerful way to block immune responses, e.g., in situations as inflammatory or autoimmune responses. See also Samter, et al. (eds.) *Immunological Diseases* vols. 1 and 2, Little, Brown and Co.

Various abnormal conditions are known in different cell types which will produce IL-D80 or IL-27, e.g., as evaluated by mRNA expression by Northern blot analysis. See Berkow (ed.) *The Merck Manual of Diagnosis and Therapy*, Merck & Co., Rahway, N.J.; Thorn, et al. *Harrison's Principles of Internal Medicine*, McGraw-Hill, N.Y.; and Weatherall, et al. (eds.) *Oxford Textbook of Medicine*, Oxford University Press, Oxford. Many other medical conditions and diseases involve activation by macrophages or monocytes, and many of these will be responsive to treatment by an agonist or antagonist provided herein. See, e.g., Stites and Terr (eds.; 1991) *Basic and Clinical Immunology* Appleton and Lange, Norwalk, Conn.; and Samter, et al. (eds.) *Immunological Diseases* Little, Brown and Co. These problems should be susceptible to prevention or treatment using compositions provided herein.

IL-D80 or IL-27, antagonists, antibodies, etc., can be purified and then administered to a patient, veterinary or human. These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using IL-D80, IL-27, WSX-1/TCCR or fragments thereof can be performed to identify compounds having binding affinity to or other relevant biological effects on IL-D80 or IL-27 functions, including isolation of associated components. Subsequent biological assays can then be utilized to determine if the compound has intrinsic stimulating activity and is therefore a blocker or antagonist in that it blocks the activity of the cytokine. Likewise, a compound having intrinsic stimulating activity can activate the signal pathway and is thus an agonist in that it simulates the activity of IL-D80 or IL-27. This invention further contemplates the therapeutic use of blocking antibodies to IL-D80, IL-27, or WSX-1/TCCR as antagonists and of stimulatory antibodies as agonists. This approach should be particularly useful with other IL-D80 or IL-27 species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) *Goodman and Gilman's: The Pharmacological Bases of Therapeutics*, latest Ed., Pergamon Press; and *Remington's Pharmaceutical Sciences*, latest ed., Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous or long term administration. See, e.g., Langer (1990) *Science* 249:1527-1533.

IL-D80 or IL-27, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic. formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, topical, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds. 1993) *Pharmaceutical Dosage Forms: Parenteral Medications*, Dekker, N.Y.; Lieberman, et al. (eds. 1990) *Pharmaceutical Dosage Forms: Tablets*, Dekker, N.Y.; and Lieberman, et al. (eds. 1990) *Pharmaceutical Dosage Forms: Disperse Systems*, Dekker, N.Y. The therapy of this invention may be combined with or used in association with other agents, e.g., other cytokines, including IL-12, or its antagonists.

Both naturally occurring and recombinant forms of the IL-D80 or IL-27s of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, which describes means for testing of binding affinity by a plurality of defined polymers synthesized on a solid substrate. The development of suitable assays can be greatly facilitated by the availability of large amounts of purified, soluble IL-D80 or IL-27 as provided by this invention.

Other methods can be used to determine the critical residues in IL-D80 or IL-27 receptor interactions. Mutational analysis can be performed, e.g., see Somoza, et al. (1993) *J. Exptl. Med.* 178:549-558, to determine specific residues critical in the interaction and/or signaling. PHD (Rost and Sander (1994) *Proteins* 19:55-72) and DSC (King and Sternberg (1996) *Protein Sci.* 5:2298-2310) can provide secondary structure predictions of α-helix (H), β-strand (E), or coil (L). Helices A and D are most important in receptor interaction, with the D helix the more important region. Boundaries for the various helices are indicated above. Surface exposed residues would affect receptor binding, while embedded residues would affect general structure.

For example, antagonists can normally be found once the antigen has been structurally defined, e.g., by tertiary structure data. Testing of potential interacting analogs is now possible upon the development of highly automated assay methods using a purified IL-D80 or IL-27. In particular, new agonists and antagonists will be discovered by using screening techniques described herein. Of particular importance are compounds found to have a combined binding affinity for a spectrum of IL-D80 or IL-27 molecules, e.g., compounds which can serve as antagonists for species variants of IL-D80 or IL-27.

One method of drug screening utilizes eukaryotic or prokaryotic host cells which are stably transformed with recombinant DNA molecules expressing an IL-D80 or IL-27. Cells may be isolated which express an IL-D80 or IL-27 in isolation from other molecules. Such cells, either in viable or fixed form, can be used for standard binding partner binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses.

Another technique for drug screening involves an approach which provides high throughput screening for compounds having suitable binding affinity to an IL-D80 or IL-27 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified IL-D80 or IL-27, and washed. The next step involves detecting bound IL-D80 or IL-27.

Rational drug design may also be based upon structural studies of the molecular shapes of the IL-D80 or IL-27 and other effectors or analogs. Effectors may be other proteins which mediate other functions in response to binding, or other proteins which normally interact with IL-D80 or IL-27, e.g., a receptor. One means for determining which sites interact with specific other proteins is a physical structure determination, e.g., x-ray crystallography or 2 dimensional NMR techniques. These will provide guidance as to which amino acid residues form molecular contact regions, as modeled, e.g., against other cytokine-receptor models. For a detailed description of protein structural determination, see, e.g., Blundell and Johnson (1976) *Protein Crystallography*, Academic Press, New York.

IX. Kits

This invention also contemplates use of IL-D80 or IL-27 proteins, fragments thereof, peptides, and their fusion products in a variety of diagnostic kits and methods for detecting the presence of another IL-D80 or IL-27 or binding partner. Typically the kit will have a compartment containing either a defined IL-D80 or IL-27 peptide or gene segment or a reagent which recognizes one or the other, e.g., IL-D80 or IL-27 fragments or antibodies.

A kit for determining the binding affinity of a test compound to an IL-D80 or IL-27 would typically comprise a test compound; a labeled compound, for example a binding partner or antibody having known binding affinity for IL-D80 or IL-27; a source of IL-D80 or IL-27 (naturally occurring or recombinant); and a means for separating bound from free labeled compound, such as a solid phase for immobilizing the molecule. Once compounds are screened, those having suitable binding affinity to the antigen can be evaluated in suitable biological assays, as are well known in the art, to determine whether they act as agonists or antagonists to the IL-D80 or IL-27 signaling pathway. The availability of recombinant IL-D80 or IL-27 polypeptides also provide well defined standards for calibrating such assays.

A preferred kit for determining the concentration of, e.g., an IL-D80 or IL-27 in a sample would typically comprise a labeled compound, e.g., binding partner or antibody, having known binding affinity for the antigen, a source of cytokine (naturally occurring or recombinant) and a means for separating the bound from free labeled compound, e.g., a solid phase for immobilizing the IL-D80 or IL-27. Compartments containing reagents, and instructions, will normally be provided.

Antibodies, including antigen binding fragments, specific for the IL-D80 or IL-27 or fragments are useful in diagnostic applications to detect the presence of elevated levels of IL-D80 or IL-27 and/or its fragments. Such diagnostic assays can employ lysates, live cells, fixed cells, immunofluorescence, cell cultures, body fluids, and further can involve the detection of antigens related to the antigen in serum, or the like. Diagnostic assays may be homogeneous (without a separation step between free reagent and antigen-binding partner complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol*. 70:1-525; Harlow and Lane (1980) *Antibodies: A Laboratory Manual*, CSH Press, N.Y; and Coligan, et al. (eds. 1993) *Current Protocols in Immunology*, Greene and Wiley, N.Y.

Anti-idiotypic antibodies may have similar use to diagnose presence of antibodies against an IL-D80 or IL-27, as such may be diagnostic of various abnormal states. For example, overproduction of IL-D80 or IL-27 may result in production of various immunological reactions which may be diagnostic of abnormal physiological states, particularly in proliferative cell conditions such as cancer or abnormal activation or differentiation. Moreover, the distribution pattern available provides information that the cytokine is expressed in pancreatic islets, suggesting the possibility that the cytokine may be involved in function of that organ, e.g., in a diabetes relevant medical condition.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled IL-D80 or IL-27 is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the binding partner, test compound, IL-D80 or IL-27, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free IL-D80 or IL-27, or alternatively the bound from the free test compound. The IL-D80 or IL-27 can be immobilized on various matrixes followed by washing. Suitable matrixes include plastic such as an ELISA plate, filters, and beads. See, e.g., Coligan, et al. (eds. 1993) *Current Protocols in Immunology*, Vol. 1, Chapter 2, Greene and Wiley, NY. Other suitable separation techniques include, without limitation, the fluorescein antibody magnetizable particle method described in Rattle, et al. (1984) *Clin. Chem*. 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-D80 or IL-27. These sequences can be used as probes for detecting levels of the IL-D80 or IL-27 message in samples from patients suspected of having an abnormal condition, e.g., inflammatory or autoimmune. Since the cytokine may be a marker or mediator for activation, it may be useful to determine the numbers of activated cells to determine, e.g., when additional therapy may be called for, e.g., in a preventative fashion before the effects become and progress to significance. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci*. 79:4381-4385; Caskey (1987) *Science* 236:962-967; and Wilchek et al. (1988) *Anal. Biochem*. 171:1-32.

Diagnostic kits which also test for the qualitative or quantitative expression of other molecules are also contemplated. Diagnosis or prognosis may depend on the combination of multiple indications used as markers. Thus, kits may test for combinations of markers. See, e.g., Viallet, et al. (1989) *Progress in Growth Factor Res*. 1:89-97. Other kits may be used to evaluate other cell subsets.

X. Isolating an IL-D80 or IL-27 Receptor

Having isolated a ligand of a specific ligand-receptor interaction, methods exist for isolating the receptor. See, Gearing, et al. (1989) *EMBO J*. 8:3667-3676. For example, means to label the IL-D80 or IL-27 cytokine without interfering with the binding to its receptor can be determined. For example, an affinity label can be fused to either the amino- or carboxyl-terminus of the ligand. Such label may be a FLAG epitope tag, or, e.g., an Ig or Fc domain. An expression library can be screened for specific binding of the cytokine, e.g., by cell sorting, or other screening to detect subpopulations which express such a binding component. See, e.g., Ho, et al. (1993) *Proc. Nat'l Acad. Sci. USA* 90:11267-11271; and Liu, et al. (1994) *J. Immunol*. 152:1821-29. Alternatively, a panning method may be used. See, e.g., Seed and Aruffo (1987) *Proc. Nat'l Acad. Sci. USA* 84:3365-3369.

Protein cross-linking techniques with label can be applied to isolate binding partners of the IL-D80 or IL-27 cytokine. This would allow identification of proteins which specifically interact with the cytokine, e.g., in a ligand-receptor. like manner. It has been shown, as noted below, that the IL-27 composite cytokine binds at least to an IL-12R-like subunit known as WSX-1/TCCR.

FACS analysis of detectably stained IL-D80, EBI3, and WSX-1/TCCR molecules led to the finding that these molecules are components in a receptor subunit/ligand complex. Specifically, the composite cytokine of E-tagged hIL-D80 (hIL-D80E) and F-tagged (FLAG-tagged) hEBI3 (FhEBI3) binds to Baf3 cells expressing an F-tagged version of WSX-1/TCCR, also referred to as hNR30. The cells were stained using anti-E mAb and a PE-conjugated anti-mouse Fab$_2$ fragment. Co-immunoprecipitation experiments also indicated that hIL-27 could be immunoprecipitated with R-tagged (RGSH$_6$-tagged) soluble WSX-1/TCCR (shNR30R). Alternatively, shNR30R could be co-immunoprecipitated in the presence of hIL-D80E/FhEBI3 complex using anti-E or anti-F mAbs. These experiments establish that WSX-1/TCCR is a receptor component of the IL-27 composite cytokine. Recent evidence shows that disrupting the WSX-1/TCCR gene in mice results in lowered expression of IFNγ, which is a critical cytokine in the mediation of pro-inflammatory functions. These mice were unable to mount a Th1 response (See, e.g., Chen, et al. (2000) *Nature* 407:916-920).

Experimental data indicates a possible role for the IL-27 composite cytokine in driving an inflammatory response. The expression profile of EBI3 and IL-D80 overlaps in monocytes, macrophages, and dendritic cells, indicating that the composite cytokine is primarily produced by antigent presenting cells (APCs) of the immune system. EBI3 has been shown to be upregulated in colonic tissue of patients suffering from gut inflammation disorders, e.g., ulcerative colitis, suggesting that the composite cytokine may also be involved.

Taken together the above indicates a role for the composite cytokine and its associated receptor subunit WSX-1/TCCR in inflammatory responses. Therefore antagonizing the function of any of the components in the receptor subunit:ligand complex should have a beneficial effect in inflammatory diseases, e.g., inflammatory bowel disease, rheumatoid arthritis, etc.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1-3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds. 1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1995 and supplements) *Current Protocols in Protein Science* John Wiley and Sons, New York, N.Y.; P. Matsudaira (ed. 1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) *QIAexpress: The High Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunology* vols. 1-4, Blackwell Science;

Coligan (1991) *Current Protocols in Immunology* Wiley/Greene, NY; and *Methods in Enzymology* vols. 70, 73, 74, 84, 92, 93, 108, 116, 121, 132, 150, 162, and 163. Cytokine assays are described, e.g., in Thomson (ed. 1998) *The Cytokine Handbook* (3d ed.) Academic Press, San Diego; Mire-Sluis and Thorpe (1998) *Cytokines* Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

Assays for vascular biological activities are well known in the art. They will cover angiogenic and angiostatic activities in tumor, or other tissues, e.g., arterial smooth muscle proliferation (see, e.g., Koyoma, et al. (1996) *Cell* 87:1069-1078), monocyte adhesion to vascular epithelium (see McEvoy, et al. (1997) *J. Exp. Med.* 185:2069-2077), etc. See also Ross (1993) *Nature* 362:801-809; Rekhter and Gordon (1995) *Am. J. Pathol.* 147:668-677; Thyberg, et al. (1990) *Atherosclerosis* 10:966-990; and Gumbiner (1996) *Cell* 84:345-357.

Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melarned, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (I1993) *Handbook of Flow Cytometry Methods* Wiley-Liss, New York, N.Y.

II. Cloning of Human IL-D80

The sequences of primate, e.g., human, genes are provided in SEQ ID NO: 1, 3, 5, and 7. These sequences are derived from a sequence database. These sequences allow preparation of PCR primers, or probes, to determine cellular distribution of the gene. These sequences allow isolation of genomic DNA which encode the message.

Using the probe or PCR primers, various tissues or cell types are probed to determine cellular distribution. PCR products are cloned using, e.g., a TA cloning kit (Invitrogen). The resulting cDNA plasmids- are sequenced from both termini on an automated sequencer (Applied Biosystems).

A structural alignment of available IL-6 family cytokine folds (CNTF, LIF, IL-6, OSM and GCSF) from FSSP (see, e.g., Holm and Sander (1998) *Nucleic Acids Res*. 26:316-319 was profile-aligned to other sequences (including distant species variants of the aforementioned cytokines, plus CT-1, GPA and viral IL-6's) with Clustal X (see, e.g., Thompson, et al. (1997) *Nucleic Acids Res*. 25:4876-4882) with some manual adjustment. A weighted profile (see, e.g., Thompson, et al. (1994) *Nucleic Acids Res*. 22:4673-4680) of the most conserved region of the fold, the C-terminal D-helix segment, a ~40 amino acid block, was created. Fast scans of sequence databases on a Bioccelerator machine (Compugen, Tel Aviv, Israel) with the Profilesearch program (Gribskov et al., 1987) identified human EST AI085007, mouse EST AA266872 and eventually,the identification of a novel hemopoietic cytokine. The cytokine was initially referred to as IL-D80, but is also known as p28 according to its apparent molecular mass as determined by SDS-PAGE.

III. Cellular Expression of IL-D8 or IL-27

An appropriate probe or primers specific for cDNA encoding primate IL-D80 or IL-27 are prepared. Typically, the probe is labeled, e.g., by random priming.

Southern Analysis: DNA (5 µg) from a primary amplified cDNA library was digested with appropriate restriction enzymes to release the inserts, run on a 1% agarose gel and transferred to a nylon membrane (Schleicher and Schuell, Keene, N.H.).

Samples for human mRNA isolation may include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); CD28-T cell clone; Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNF_12 days, resting (D101); DC 70% CD1a+, from CD34+ GM-CSF, TNF_12 days, activated with PMA and ionomycin for 1 hr (D102); DC 70% CD1a+, from CD34+ GM-CSF, TNF_12 days, activated with PMA and ionomycin for 6 hr (D103); DC 95% CD1a+, from CD34+ GM-CSF, TNF_12 days FACS sorted, activated with PMA and ionomycin for 1, 6 h pooled (D104); DC 95% CD14+, ex CD34+ GM-CSF, TNF_12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); epithelial cells, unstimulated; epithelial cells, IL-1β activated; lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102).

A rodent counterpart, e.g., mouse, has been identified, and its distributions will be similarly evaluated. Samples for mouse mRNA isolation can include: resting mouse fibroblastic L cell line (C200); Braf:ER (Braf fusion to estrogen receptor) transfected cells, control (C201); Mel14+ naive T cells from spleen, resting (T209); Mel14+ naive T cells from spleen, stimulated with IFN_, IL-12, and anti IL-4 to polarize to TH1 cells, exposed to IFNγ and IL-4 for 6, 12, 24 h, pooled (T210); Mel14+ naive T cells from spleen, stimulated with IL-4 and anti IFNγ to polarize to Th2 cells, exposed to IL-4 and anti IFNγ for 6, 13, 24 h, pooled (T211); T cells, TH1 polarized (Mel14 bright, CD4+ cells from spleen, polarized for 7 days with IFN-_and anti IL-4; T200); T cells, TH2 polarized (Mel14 bright, CD4+ cells from spleen, polarized for 7 days with IL-4 and anti-IFN-_; T201); T cells, highly TH1 polarized 3× from transgenic Balb/C (see Openshaw, et al. (1995) *J. Exp. Med.* 182:1357-1367; activated with anti-CD3 for 2, 6, 24 h pooled; T202); T cells, highly TH2 polarized 3× from transgenic Balb/C (activated with anti-CD3 for 2, 6, 24 h pooled (T203); T cells, highly TH1 polarized 3× from transgenic C57 bl/6 (activated with anti-CD3 for 2, 6, 24 h pooled; T212); T cells, highly TH2 polarized 3× from transgenic C57 bl/6 (activated with anti-CD3 for 2, 6, 24 h pooled; T213); T cells, highly TH1 polarized (naive CD4+ T cells from transgenic Balb/C, polarized 3× with IFN_, IL-12, and anti-IL-4; stimulated with IGIF, IL-12, and anti IL-4 for 6, 12, 24 h, pooled); CD44− CD25+ pre T cells, sorted from thymus (T204); TH1 T cell clone D1.1, resting for 3 weeks after last stimulation with antigen (T205); TH1 T cell clone D1.1, 10_g/ml ConA stimulated 15 h (T206); TH2 T cell clone CDC35, resting for 3 weeks after last stimulation with antigen (T207); TH2 T cell clone CDC35, 10_g/ml ConA stimulated 15 h (T208); unstimulated B cell line CH12 (B201); unstimulated mature B cell leukemia cell line A20 (B200); unstimulated large B cells from spleen (B202); B cells from total spleen, LPS activated (B203); metrizamide enriched dendritic cells from spleen, resting (D200); dendritic cells from bone marrow, resting (D201); unstimulated bone marrow derived dendritic cells depleted with anti B220, anti CD3, and anti Class II, cultured in GM-CSF and IL-4 (D202); bone marrow derived dendritic cells depleted with anti B220, anti CD3, and anti Class II, cultured in GM-CSF and IL-4, stimulated with anti CD40 for 1, 5 d, pooled (D203); monocyte cell line RAW 264.7 activated with LPS 4 h (M200); bone-marrow macrophages derived with GM and M-CSF (M201); bone-marrow macrophages derived with GM-CSF, stimulated with LPS, IFN_, and IL-10 for 24 h (M205); bone-marrow macrophages derived with GM-CSF, stimulated with LPS, IFN_, and anti IL-10 for 24 h (M206); peritoneal macrophages (M207); macrophage cell line J774, resting (M202); macrophage cell line J774+LPS+anti-IL-10 at 0.5, 1, 3, 6, 12 h pooled (M203); macrophage cell line J774+LPS+IL-10 at 0.5, 1, 3, 5, 12 h pooled (M204); unstimulated mast cell lines MC-9 and MCP-12 (M208); immortalized endothelial cell line derived from brain microvascular endothelial cells, unstimulated (E200); immortalized endothelial cell line derived from brain microvascular endothelial cells, stimulated overnight with TNFα (E201); immortalized endothelial cell line derived from brain microvascular endothelial cells, stimulated overnight with TNFα (E202); immortalized endothelial cell line derived from brain microvascular endothelial cells, stimulated overnight with TNFα and IL-10 (E203); total aorta from wt C57 bl/6 mouse; total aorta from 5 month ApoE KO mouse (X207); total aorta from 12 month ApoE KO mouse (X207); wt thymus (O214); total thymus, rag-1 (O208); total kidney, rag-1 (O209); total kidney, NZ B/W mouse; and total heart, rag-1 (O202). High signal was detected in the monocyte cell line RAW 264.7 activated with LPS 4 h (M200); T cells, highly TH1 polarized 3× from transgenic C57 bl/6 (activated with anti-CD3 for 2, 6, 24 h pooled; T212); and T cells, highly TH1 polarized (naive CD4+ T cells from transgenic Balb/C, polarized 3× with IFNγ, IL-12, and anti-IL-4; stimulated with IGIF, IL-12, and anti IL-4 for 6, 12, 24 h, pooled).

IV. Chromosome Mapping of IL-D80

An isolated cDNA encoding the IL-D80 is used. Chromosome mapping is a standard technique. See, e.g., BIOS Laboratories (New Haven, Conn.) and methods for using a mouse somatic cell hybrid panel with PCR. The human IL-D80 gene is located on chromosome 16p11.

V. Expression and Purification of IL-D80 or IL-27 Proteins

Multiple transfected cell lines are screened for one which expresses the cytokine at a high level compared with other cells. Various cell lines are screened and selected for their favorable properties in handling. Natural IL-D80 can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or $His_6$ segments can be used for such purification features. Alternatively, affinity chromatography may be used with specific antibodies, see below.

cDNAs encoding full length human and mouse IL-D80 were cloned into the pCDM8-E-tag vector via HindIII-XhoI (h/mp28-E). EBI3: human and mouse EBI3 were cloned into pME18S-Ig vector via EcoRI/XhoI (h/mEBI3-Ig) and the mature portion of human EBI3 into p-FLAG-CMV-1 vector via HindIII-NotI (F-hEBI3). One chain fusions EBI3/p28: HindIII-XbaI fragments were generated encoding the mature part of human or mouse EBI3, followed by the synthetic linker GSGSGGSGGSGSGKL (SEQ ID NO: 13)and by the mature coding sequence of human or mouse IL-D80 via HindIII-NotI. Fragments were inserted into pFLAG-CMV-1 (Sigma, St. Louis, Mo.) using HindIII-NotI sites.

WSX-1/TCCR: the preprotrypsin leader peptide and the FLAG-tag encoding part of p-FLAG-CMV-1 vector were deleted by PCR, instead an $RGSH_6$-tag was introduced via SalI/SmaI (pCMV-1-$RGSH_6$); the cDNA encoding the extracellular part of human WSX-1 was cloned into this vector via HindIII-SalI (soluble hWSX-1-R). In general restriction sites were introduced through the respectively used PCR primers and cDNA was amplified using standard PCR protocols. Proteins were produced via transient expression in HEK293T cells. For experiments requiring pure proteins purification was performed by affinity chromatography using the respective protein tags.

VI. Transient Transfection, Metabolic Labeling and Immunoprecipitation $1 \times 10^6$ HEK293T cells were transiently transfected with a total amount of 5 µg plasmid DNA (control vector, expression vectors encoding h/m p28-E, F-hEBI3 and mEBI3-Ig, or respective combinations). Cells were cultured for 24 hr after transfection, then metabolically labeled for 16 hr with 50 µCi/ml Pro-mix L-[$^{35}$S] in vitro cell labeling mix (Amersham Pharmacia, Piscataway, N.J.) in cysteine/methionine free MEM. Proteins were precipitated from supernatants with either anti-FLAG M2 agarose (Sigma, St. Louis, Mo.), with anti-E-tag mAb bound to protein G Sepharose® (Amersham Pharmacia), or with protein A Sepharose® (Amersham Pharmacia).

VII. Retroviral Constructs

The mature part of human and mouse WSX-1 was cloned into pMX vector via HindIII-NotI, then a sequence encoding the preprotrypsin leader peptide fused to a FLAG epitope was cloned into the vector in frame and 5' of WSX-1 via BamHI-HindIII (F-h/mWSX-1). Retrovirus obtained by transfection of BOSC23 cells was used to infect parental Ba/F3 cells and cell surface expression of the desired proteins was monitored using a FLAG-PE-staining in FACS analysis.

VIII. Isolation of Homologous IL-D80 Genes

The IL-D80 cDNA, or other species counterpart sequence, can be used as a hybridization probe to screen a library from a desired source, e.g., a primate. cell cDNA library. Many different species can be screened both for stringency necessary for easy hybridization, and for presence using a probe. Appropriate hybridization conditions will be used to select for clones exhibiting specificity of cross hybridization.

Screening by hybridization using degenerate probes based upon the peptide sequences will also allow isolation of appropriate clones. Alternatively, use of appropriate primers for PCR screening will yield enrichment of appropriate nucleic acid clones.

Similar methods are applicable to isolate either species, polymorphic, or allelic variants. Species variants are isolated using cross-species hybridization techniques based upon isolation of a full length isolate or fragment from one species as a probe.

Alternatively, antibodies raised against human IL-D80 or IL-27 will be used to screen for cells which express cross-reactive proteins from an appropriate, e.g., cDNA library. The purified protein or defined peptides are useful for generating antibodies by standard methods, as described above. Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. The resulting antibodies are used for screening, purification, or diagnosis, as described.

IX. Preparation of antibodies specific for IL-D80 or IL-27

Synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Polyclonal serum, or hybridomas may be prepared. In appropriate situations, the binding reagent is either labeled as described above, e.g., fluorescence or otherwise, or immobilized to a substrate for panning methods. Immunoselection, absorptions, and related techniques are available to prepare selective reagents, e.g., exhibiting the desired spectrum of selectivity for binding.

X. Generation and Analysis of Genetically Altered Animals

Transgenic mice can be generated by standard methods. Such animals are useful to determine the effects of deletion of the gene, in specific tissues, or completely throughout the organism. Such may provide interesting insight into development of the animal or particular tissues in various stages. Moreover, the effect on various responses to biological stress can be evaluated. See, e.g., Hogan, et al. (1995) *Manipulating the Mouse Embryo: A Laboratory Manual* (2d ed.) Cold Spring Harbor Laboratory Press.

IX. Expression/Distribution of IL-27 cDNAs from various libraries or cultured macrophages and dendritic cells were prepared as described (see, e.g., Bolin, et al. (1997) *J. Neurosci.* 17:5493-5502) and used as templates for quantitative PCR. 50 ng cDNA was analyzed for expression of human and mouse p28 and EBI3 by the fluorogenic 5'-nuclease PCR assay (see, e.g., Holland, et al. (1991) *Proc. Natl. Acad. Sci.* 88:7276-7280) using the ABI Prism 7700 Sequence Detection System (Perkin-Elmer, Foster City, Calif.). Analysis of cDNA samples was corrected for expression of 18S rRNA using a VIC labeled probe (Perkin-Elmer) in multiplex reactions.

Analysis of a large panel of human and mouse cDNA libraries by real time quantitative PCR showed that expression of IL-D80 and EBI3 is highly restricted. Both mRNAs are primarily found in cells of myeloid lineage in human as well as mouse. Highest levels of human mRNA's were found in LPS activated monocytes and monocyte derived dendritic cells (DCs). A very high level of hEBI3 MRNA but not hp28, was seen in placenta. This observation is in agreement with earlier reports of high levels of EBI3 protein in placental syncytiotrophoblasts [Devergne, 1997 #3]. A similar pattern emerged when we analyzed the expression profile of mouse IL-D80 and EBI3. Although mEBI3 was also expressed in some T and B cell libraries, highest levels of both mIL-D80 and mEBI3 was in activated macrophages.

Since antigen presenting cells are also the primary source of IL-12 (see, e.g., Macatonia, et al. (1995) *J. Immunol.* 154:5071-5079) we studied the kinetics of production of IL-12p35, IL-12p40, IL-D80 and EBI3 by monocyte derived DCs stimulated with LPS. Human monocytes were isolated from peripheral blood, stimulated with GM-CSF and IL-4 for 7 days to obtain immature DCs. Subsequently, these CD14+ CD11c+DCs were activated by LPS for various time intervals and mRNA levels of IL-12p35, IL-12p40, IL-D80 and EBI3 were analyzed by real time quantitative PCR. Despite substantial variations in the absolute amounts of PCR product from donor to donor and from protein to protein, the kinetics recorded were consistent and revealed subtle differences between the four investigated proteins. After an initial lag phase, message levels for IL-12p35 and IL-12p40 rapidly increased and consistently peaked between 8 and 14 hours of LPS stimulation, then dropped back to background level after 24 hours. The profiles for the two subunits of IL-12 are essentially superimposable. A very transient expression was also observed for IL-D80, although maximal message levels were already found after 3-6 hours. Similar to IL-12, mRNA levels for p28 declined to background levels after 24 hours. In contrast, EBI3 showed less transient expression although its transcription was also rapidly induced as early as 3 h after LPS stimulus. Reaching maximal EBI3 mRNA levels between 12 and 24 hours, after 72 hours EBI3 message in all three donors was still above the unstimulated background levels.

X. Transient Transfection, Metabolic Labeling, and Immunoprecipitation

Appropriate host cells were transiently transfected with empty vectors or expression vectors encoding hIL-D80E (E=E-tagged) and/or FhEBI3 (F=FLAG-tagged). Cells were cultured to 24 hrs. and then metabolically labeled for 16 hrs with 50 µCi/ml PRO-MIX L-[$^{35}$S] in vitro cell labeling mix (Amersham Pharmacia) in cysteine/methionine free MEM cell culture media. Proteins were precipitated from 300 mL supernatant with either the anti-His5 mAb or anti-E or anti-F mAb. The IL-12R like subunit, WSX-1/TCCR, was also detectably labeled with RGSH$_6$-tag (shNR30R) and immunoprecipated as above.

XI. 2D-PAGE

Purified labeled IL-27 composite cytokine or IL-27-WSX-1/TCCR complex were run on a nonreducing 10% NUPAGE gel in MES running buffer (Novex, San Diego, Calif.). Appropriate lanes were excised, reduced in sample buffer containing DTT, laid horizontally on two-well 10% gels, and run reduced in a second dimension. One gel was silver stained (Daiichi, Tokyo, Japan) while the other was blotted to a PVDF membrane and developed using appropriate mAbs. It was found that hIL-80E could be co-immunoprecipitated with shNR30R in the presence of FhEBI3 using the anti-His$_6$ mAb. Alternatively, shNR30R could be immunoprecipated in the presence of hIL-80E and FhEBI3 using the anti-E mAb or anti-F mAb.

XII. Biological Effects of IL-27

A. Naive Human and Mouse T cells

CD4+CD45RB$^{high}$ or CD4+CD45RB$^{low}$ T cell subsets were purified from the spleen and mesenteric lymph nodes of >6 month old IL-10-/-C57/B6 N12 mice as described (Davidson et al. (1998) *J. Immunol.* 161:3143-3149). Cells were fractionated into CD4+CD45RB$^{high}$ and CD4+CD45RB$^{low}$ cell populations by two color sorting on a FACSTAR plus (Becton Dickinson, San Jose, Calif.). All populations were >99% pure upon reanalysis. CD4+CD45RB$^{high}$ or CD4+ CD45RB$^{low}$ were put into a proliferation assay with plate bound anti-CD3 (145.2C11) stimulation as described (Davidson et al. (1998) *J. Immunol.* 161:3143-3149). Additions to the growth media included anti-IL-2 Mab (JES6-1A12) 100 µg/ml, and cytokines as indicated. Cells were incubated for 5 days in a humidified chamber (37° C., 5% CO$_2$) with [$^3$H] TdR (Amersham) added at a final concentration of 1 µCi/well for the last 24 h of incubation.

Sorted mouse naive T cells (CD4+CD45RB$^{high}$) and memory/activated T cells (CD4+CD45RB$^{low}$) were stimulated with CD3 mAb for four days in the presence of anti-IL-12 antibody and various amounts of mIL-27. Upon stimulation, naive T cells, but not memory T cells, showed a strong proliferative response. Proliferation was augmented by addition of IL-12 at saturating levels, revealing synergy between IL-27 and IL-12 on unstimulated T cells. IL-27 was able to act as a strong expansion factor for anti-CD3, anti-CD28 activated naive T cells in the absence of IL-12.

FACS purified CD45RA and CD45RO T cells (purity >99%) were cultured at a density of 4×10$^4$ cells/well in a 96-well plate previously coated with anti-CD3 antibody at 10 µg/ml and soluble anti-CD28 at 1 µg/ml with or without IL-26/EBI3. Anti-hIL-2 mAb 17H12 and anti-hIL-2R mAb B-B10 (Diaclone, Besabcibm France) were added at 10 µg/ml where indicated. IL-27 was also able to induce proliferation of FACS sorted human CD45RA naive T cells isolated from peripheral blood mononuclear cells (PBMC). Similar to the results with mouse naive T cells, IL-27 induced strong proliferation of CD3/CD28 naive T cells in the presence of anti-IL-2. This response was enhanced by the addition of IL-12. No response was seen with IL-27 treated CD45RO memory cells.

Thus, IL-27 dependent. proliferation can be enhanced by costimulatory signals through either CD28 or the IL-12 receptors. IL-27 induced proliferation is dependent on simultaneous crosslinking of CD3/TCR, since no proliferation was observed in the absence of CD3 activation (data not shown). The same maximal proliferative response could be induced by stimulation with conditioned medium of p28/EBI3 co-transfected cells (data not shown). To compare the abilities of IL-27 and IL-12 to induce proliferation of naïve CD4+ T cells, FACS sorted mouse CD4+CD45Rbhigh T cells were pre-cultured with plate bound anti-CD3 mAb, and either IL-27 or IL-12 were titrated into the cultures. IL-27 proved to be a much more potent proliferative stimulus for these cells (FIG. 4C).

Thus, IL-27 dependent proliferation can be enhanced by costimulatory signals through either CD28 or the IL-12 receptors. IL-27 induced proliferation is dependent on simultaneous crosslinking of CD3/TCR, since no proliferation was observed in the absence of CD3 activation. The same maximal proliferative response could be induced by stimulation with conditioned medium of IL-27 co-transfected cells. To compare the abilities of IL-27 and IL-12 to induce proliferation of naïve CD4+ T cells, FACS sorted mouse CD4+ CD45RB$^{high}$ T cells were pre-cultured with plate bound anti-CD3 mAb, and either IL-27 or IL-12 were titrated into the cultures. IL-27 proved to be a much more potent proliferative stimulus for these cells.

B. Induction of IFN-γ

The ability of human and mouse IL-27 to induce the production of IFNγ_in the presence of a neutralizing anti-IL-2 mAb, with costimulation via anti-CD3 or anti-CD3/anti-CD28 and both in the absence and presence of IL-12 was measured. In this assay neither hIL-27 nor hIL-12 by itself induced IFNγ_production in anti-CD3 or anti-CD3/anti-CD28 activated CD4$^+$CD45RA T cells. IFNγ production was only observed in the presence of both cytokines indicating strong synergy between IL-27 and IL-12.

Sorted mouse CD4$^+$CD45RB$^{high}$ naïve T cells were stimulated for 4 days with anti-CD3 mAb alone or with anti-CD3 mAb/anti-CD28 mAb and saturating amounts of IL-27 and IL-12. In the absence of anti-CD28 costimulation neither IL-27 nor IL-12 by itself was capable of inducing substantial amounts of IFNγ_. However, the combination of IL-27 and IL-12 induced up to about 300 ng/ml of IFNγ_. With anti-CD3/anti-CD28 costimulation, IL-27 as well as IL-12 were capable of inducing IFNγ production. The combination of both factors led to an additive effect with IFNγ levels up to 550 ng/ml.

C. IL-27 does not drive Th2 polarization of naïve T cells

Sorted mouse CD4$^+$CD45RBhigh T cells were cultured with plate bound anti-CD3 and anti-CD28 in the presence of IL-4 and IL-27. Including IL-27 in the cultures led to a decreased IL-13 production both in the absence and presence of IL-4. Thus, while inducing a strong Th1 response, IL-27 does not appear to promote Th2 polarization.

D. IL-27 binds to WSX-1/TCCR

Because of the relationship between IL-27 and the IL-6/IL-12 family, the search for the signaling receptors was concentrated on this family. Members of this family were introduced into BaF3 cells and tested for binding to IL-27. Of the receptors tested only Ba/F3 cells expressing the orphan cytokine receptor WSX-1/TCCR (see, e.g., Sprecher, et al. (1998) *Biochem. Biophys. Res. Comm.* . 246:82-90; and Chen, et al. (2000) *Nature* 407:916-920) showed binding to tagged IL-27. BaF3 cells infected with retroviral constructs expressing either F-tagged human or mouse WSX-1 cDNA (F-hWSX-1 or F-mWSX-1) showed cellular staining using anti-FLAG mAb. Cells expressing F-hWSX-1 were then incubated with either hEBI3-Ig alone or with coexpressed hIL-D80-E and EBI3-Ig for two hours. Heterodimeric IL-D80/EBI3 bound to WSX-1 while EBI3-Ig itself showed no detectable binding. Similarly, only the combination of mIL-D80-E and mEBI3-Ig provided a detectable interaction with mWSX-1-expressing BaF3 cells, whereas the two individual proteins were not able to do so. Incubation of independently expressed mIL-D80-E and mEBI3-Ig with F-mWSX-1 expressing BaF3 cells also led to cellular staining. Untransfected control cells were not stained by IL-D80/EBI3, demonstrating the specificity of the observed interactions.

These results were confirmed by co-immunoprecipitation experiments using a soluble extracellular form of hWSX-1 with a C-terminal RSGH$_6$-tag (R). Proteins from supernatants of transiently transfected HEK293T cells containing F-hEBI3 or coexpressed hILD80-E/F-hEBI3 were immunoprecipitated using either FLAG M2-agarose, protein G Sepharose®-coupled anti-E-tag mAb(Amersham Pharmacia, Piscataway, N.J.) or protein G Sepharose®-coupled anti-H$_5$ mAb. The primary precipitates were washed and then incubated with HEK293T cell supernatants containing shWSX-1-R. Secondary precipitates were separated by SDS-PAGE and subjected to western blot. Precipitated proteins were visualized by enhanced chemiluminescence (ECL) 5 using antibodies against the respective protein tags. Only when all three proteins were present (hIL-D80-E, F-hEBI3 and shWSX-1-R), immunoprecipitation of one protein brought down both other components independently of the immunoprecipitating antibody used. The same co-immunoprecipitation experiment using the respective mouse orthologues had similar results.

To address the question if WSX-1 was sufficient to mediate IL-27 signal transduction, proliferation of BaF3 cells expressing human or mouse WSX-1 was tested. These cells proliferate in response to IL-3 but did not proliferate in response to IL-27. Thus WSX-1 appears to be required but not sufficient for IL-27 mediated signal transduction. The identification of additional IL-27 signal transducing receptor subunits is currently in progress.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated polypeptide comprising the amino acid sequence of SEQ ID NO:2.
2. The isolated polypeptide of claim 1, wherein the polypeptide is chemically modified.
3. The isolated polypeptide of claim 2, wherein the chemical modification is glycosylation or phosphorylation.

* * * * *

UNITED STATES PATENT AND TRADEMARK OFFICE
CERTIFICATE OF CORRECTION

PATENT NO. : 7,579,440 B2 Page 1 of 1
APPLICATION NO. : 10/777790
DATED : August 25, 2009
INVENTOR(S) : Timans et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 858 days.

Signed and Sealed this

Fourteenth Day of September, 2010

David J. Kappos
*Director of the United States Patent and Trademark Office*

SEQUENCE LISTING

```
<160> NUMBER OF SEQ ID NOS: 13

<210> SEQ ID NO 1
<211> LENGTH: 1213
<212> TYPE: DNA
<213> ORGANISM: Homo sapiens

<400> SEQUENCE: 1
cactggccca cgctgaagat aggggacttg agttccagtc ttccttctgc taccgaccgg      60
ctttgtgacc ttgaacaaga cttcccctcc ctgattccat cctcatgtca catctgaagc     120
ctccaacttc tgtcactgag ctcaggattc ccaggcaagc ccacggagtg ccccacaggg    180
```

```
tcagagccgt aacaggactt ggaaaataac ccgaaaattg ggctcagcct gttgctgctt    240
cccttgctcc tggttcaagc tggtgtctgg ggattcccaa ggcccccagg gaggcccag     300 ctgagcctgc aggagctgcg gagggagttc acagtcagcc tgcatctcgc aggaagctg     360 ctctccgagg ttcggggcca ggcccaccgc tttgcggaat ctcacctgcc aggagtgaac    420
ctgtacctcc tgcccctggg agagcagctc cctgatgttt ccctgacctt ccaggcctgg    480
cgccgcctct ctgacccgga gcgtctctgc ttcatctcca ccacgcttca gcccttccat    540
gccccgctgg gagggctggg acccagggc cgctggacca acatggagag gatgcagctg    600
tgggccatga ggctggacct ccgcgatctg cagcggcacc tccgcttcca ggtgctggct    660
gcaggattca acctcccgga ggaggaggag gaggaagagg aggaggagga ggaggagagg    720
aaggggctgc tcccaggggc actgggcagc gccttacagg gccgggccca ggtgtcctgg    780
ccccagctcc tctccaccta ccgcctgctg cactccttgg agctcgtctt atctcgggcc    840
gtgcgggagt gctgctgct gtccaaggct gggcactcag tctggccctt ggggttccca    900
acattgagcc cccagccctg atcggtggct tcttagcccc ctgcccccca cccttagaa    960 ctttaggact ggagtcttgg catcagggca gccttcgcat catcagcctt ggacaaggga   1020
gggctcttcc agcccctgc cccaggccct acccagtaac tgaaagcccc tctggtcctc   1080
gccagctatt tatttcttgg atatttattt attgttagg gagatgatgg tttatttatt    1140
gtcttggggc ccgatggtcc tcctcgggcc aagcccccat gctgggtgcc caataaagca   1200
ctctcatcca aaa                                                      1213

<210> SEQ ID NO 2
<211> LENGTH: 242
<212> TYPE: PRT
<213> ORGANISM: Homo sapiens

<400> SEQUENCE: 2

Gln Asp Leu Glu Asn Asn Pro Lys Ile Gly Leu Ser Leu Leu Leu
1               5                   10                  15

Pro Leu Leu Leu Val Gln Ala Gly Val Trp Gly Phe Pro Arg Pro Pro
            20                  25                  30

Gly Arg Pro Gln Leu Ser Leu Gln Glu Leu Arg Arg Glu Phe Thr Val
        35                  40                  45

Ser Leu His Leu Ala Arg Lys Leu Leu Ser Glu Val Arg Gly Gln Ala
    50                  55                  60

His Arg Phe Ala Glu Ser His Leu Pro Gly Val Asn Leu Tyr Leu Leu
65                  70                  75                  80

Pro Leu Gly Glu Gln Leu Pro Asp Val Ser Leu Thr Phe Gln Ala Trp
                85                  90                  95

Arg Arg Leu Ser Asp Pro Glu Arg Leu Cys Phe Ile Ser Thr Thr Leu
            100                 105                 110

Gln Pro Phe His Ala Pro Leu Gly Gly Leu Gly Thr Gln Gly Arg Trp
        115                 120                 125

Thr Asn Met Glu Arg Met Gln Leu Trp Ala Met Arg Leu Asp Leu Arg
    130                 135                 140

Asp Leu Gln Arg His Leu Arg Phe Gln Val Leu Ala Ala Gly Phe Asn
145                 150                 155                 160

Leu Pro Glu Glu Glu Glu Glu Glu Glu Glu Glu Glu Glu Glu Glu Arg
                165                 170                 175

Lys Gly Leu Leu Pro Gly Ala Leu Gly Ser Ala Leu Gln Gly Pro Ala
            180                 185                 190
```

-continued

```
Gln Val Ser Trp Pro Gln Leu Leu Ser Thr Tyr Arg Leu Leu His Ser
            195                 200                 205

Leu Glu Leu Val Leu Ser Arg Ala Val Arg Glu Leu Leu Leu Leu Ser
        210                 215                 220

Lys Ala Gly His Ser Val Trp Pro Leu Gly Phe Pro Thr Leu Ser Pro
225                 230                 235                 240

Gln Pro

<210> SEQ ID NO 3
<211> LENGTH: 1098
<212> TYPE: DNA
<213> ORGANISM: Mus musculus
<220> FEATURE:
<221> NAME/KEY: misc_feature
<222> LOCATION: (1)..(1)
<223> OTHER INFORMATION: Unidentified base.
<220> FEATURE:
<221> NAME/KEY: misc_feature
<222> LOCATION: (1)..(7)
<223> OTHER INFORMATION: Unidentified base at position 1 and position 7.

<400> SEQUENCE: 3
nccaagntgg tacgcctgca ggtaccggtc cggaattccc gggtcgaccc acgcgtccgg        60
ggccaggtga caggagacct tggctggcga ggactggaca ggcaacctgg ccaggagcag       120
gactaaacag acaaatgaag agtgtagagg gaagaggctg agaaccgagg acagtcagag       180
gaacggcaca ggggagctgg gctcagcctg ttgctgctac ccttgcttct ggtacaagct       240
ggttcctggg ggtcccaac agacccctg agccttcaag agctgcgcag ggaattcaca        300
gtcagcctgt accttgccag gaagctgctc tctgaggttc agggctatgt ccacagcttt       360
gctgaatctc gattgccagg agtgaacctg gacctcctgc ccctgggata ccatcttcct       420
aatgtttccc tgactttcca ggcatggcat cacctctctg actctgagag actctgcttc       480
ctcgctacca cacttcggcc cttccttgcc atgctgggag gctggggac ccaggggacc       540 tggaccaaca tcaagaggat gcagcaatgg agactctctc tggttcttga tgtggccctg       600
tgtgtctttc gctcacaggt gctggctgca ggattcaaat gttcaaagga ggaggaggac       660
aaggaggaag aggaagagga ggaagaagaa gaaaagaagc tgcccctagg gcgtctgggt       720
ggccccaatc aggtgtcatc ccaagtgtcc tggccccagc tgctctatac ctaccagctc       780
cttcactcca tggagcttgt cctgtctcgg gctgttcggg acctgctgct gctgtccctg       840
cccaggcgcc caggctcagc cttggagttc ctaacaccta gcttcaagcc ctgatggagt       900
gaccttccag ctcccctcct cgcccgttaa gactctaagg ctggagtctg gccaatcaca       960
ggacaggctc tagctcgttt gccttagacc aggcagggtt tcactagctc ccagccctga      1020
cccaataatt taaaagcccct ccagtcctta ccagatattt atttcttgga tatttattta      1080
tttttaagaa atggttta                                                    1098

<210> SEQ ID NO 4
<211> LENGTH: 231
<212> TYPE: PRT
<213> ORGANISM: Mus musculus

<400> SEQUENCE: 4

Gly Leu Ser Leu Leu Leu Pro Leu Leu Leu Val Gln Ala Gly Ser
1               5                  10                  15

Trp Gly Phe Pro Thr Asp Pro Leu Ser Leu Gln Glu Leu Arg Arg Glu
            20                  25                  30
```

Phe Thr Val Ser Leu Tyr Leu Ala Arg Lys Leu Leu Ser Glu Val Gln
             35                  40                  45

Gly Tyr Val His Ser Phe Ala Glu Ser Arg Leu Pro Gly Val Asn Leu
 50                  55                  60

Asp Leu Leu Pro Leu Gly Tyr His Leu Pro Asn Val Ser Leu Thr Phe
 65                  70                  75                  80

Gln Ala Trp His His Leu Ser Asp Ser Glu Arg Leu Cys Phe Leu Ala
             85                  90                  95

Thr Thr Leu Arg Pro Phe Leu Ala Met Leu Gly Gly Leu Gly Thr Gln
            100                 105                 110

Gly Thr Trp Thr Asn Ile Lys Arg Met Gln Gln Trp Arg Leu Ser Leu
            115                 120                 125

Val Leu Asp Val Ala Leu Cys Val Phe Arg Ser Gln Val Leu Ala Ala
130                 135                 140

Gly Phe Lys Cys Ser Lys Glu Glu Asp Lys Glu Glu Glu Glu
145                 150                 155                 160

Glu Glu Glu Glu Glu Lys Lys Leu Pro Leu Gly Arg Leu Gly Gly Pro
                165                 170                 175

Asn Gln Val Ser Ser Gln Val Ser Trp Pro Gln Leu Leu Tyr Thr Tyr
            180                 185                 190

Gln Leu Leu His Ser Met Glu Leu Val Leu Ser Arg Ala Val Arg Asp
            195                 200                 205

Leu Leu Leu Leu Ser Leu Pro Arg Arg Pro Gly Ser Ala Leu Glu Phe
            210                 215                 220

Leu Thr Pro Ser Phe Lys Pro
225                 230

<210> SEQ ID NO 5
<211> LENGTH: 732
<212> TYPE: DNA
<213> ORGANISM: Homo sapiens

<400> SEQUENCE: 5
atgggccaga cggcaggcga ccttggctgg cggctcagcc tgttgctgct tcccttgctc      60
ctggttcaag ctggtgtctg gggattccca aggcccccag ggaggcccca gctgagcctg     120
caggagctgc ggagggagtt cacagtcagc ctgcatctcg ccaggaagct gctctccgag     180
gttcggggcc aggcccaccg ctttgcggaa tctcacctgc aggagtgaa cctgtacctc      240 ctgcccctgg gagagcagct ccctgatgtt ccctgacct tccaggcctg cgccgcctc       300 tctgacccgg agcgtctctg cttcatctcc accacgcttc agcccttcca tgccccgctg     360
ggagggctgg ggacccaggg ccgctggacc aacatggaga ggatgcagct gtgggccatg     420
aggctggacc tccgcgatct gcagcggcac ctccgcttcc aggtgctggc tgcaggattc     480
aacctcccgg aggaggagga ggaggaagag gaggaggagg aggaggagag gaagggggtg     540
ctcccagggg cactgggcag cgccttacag ggcccggccc agtgtcctg gccccagctc      600 ctctccacct accgcctgct gcactccttg gagctcgtct atctcgggc cgtgcgggag      660 ttgctgctgc tgtccaaggc tgggcactca gtctggccct tggggttccc aacattgagc     720
ccccagccct ga                                                         732

<210> SEQ ID NO 6
<211> LENGTH: 243
<212> TYPE: PRT
<213> ORGANISM: Homo sapiens

<400> SEQUENCE: 6

```
Met Gly Gln Thr Ala Gly Asp Leu Gly Trp Arg Leu Ser Leu Leu Leu
1               5                   10                  15
Leu Pro Leu Leu Leu Val Gln Ala Gly Val Trp Gly Phe Pro Arg Pro
            20                  25                  30
Pro Gly Arg Pro Gln Leu Ser Leu Gln Glu Leu Arg Arg Glu Phe Thr
        35                  40                  45
Val Ser Leu His Leu Ala Arg Lys Leu Leu Ser Glu Val Arg Gly Gln
    50                  55                  60
Ala His Arg Phe Ala Glu Ser His Leu Pro Gly Val Asn Leu Tyr Leu
65                  70                  75                  80
Leu Pro Leu Gly Glu Gln Leu Pro Asp Val Ser Leu Thr Phe Gln Ala
                85                  90                  95
Trp Arg Arg Leu Ser Asp Pro Glu Arg Leu Cys Phe Ile Ser Thr Thr
            100                 105                 110
Leu Gln Pro Phe His Ala Pro Leu Gly Gly Leu Gly Thr Gln Gly Arg
        115                 120                 125
Trp Thr Asn Met Glu Arg Met Gln Leu Trp Ala Met Arg Leu Asp Leu
    130                 135                 140
Arg Asp Leu Gln Arg His Leu Arg Phe Gln Val Leu Ala Ala Gly Phe
145                 150                 155                 160
Asn Leu Pro Glu Glu Glu Glu Glu Glu Glu Glu Glu Glu Glu Glu Glu
                165                 170                 175
Arg Lys Gly Leu Leu Pro Gly Ala Leu Gly Ser Ala Leu Gln Gly Pro
            180                 185                 190
Ala Gln Val Ser Trp Pro Gln Leu Leu Ser Thr Tyr Arg Leu Leu His
        195                 200                 205
Ser Leu Glu Leu Val Leu Ser Arg Ala Val Arg Glu Leu Leu Leu Leu
    210                 215                 220
Ser Lys Ala Gly His Ser Val Trp Pro Leu Gly Phe Pro Thr Leu Ser
225                 230                 235                 240
Pro Gln Pro
```

<210> SEQ ID NO 7
<211> LENGTH: 991
<212> TYPE: DNA
<213> ORGANISM: Mus musculus
<220> FEATURE:
<221> NAME/KEY: misc_feature
<222> LOCATION: (1)..(1)
<223> OTHER INFORMATION:
<220> FEATURE:
<221> NAME/KEY: misc_feature
<222> LOCATION: (7)..(7)
<223> OTHER INFORMATION:

<400> SEQUENCE: 7

```
atgggccaga cggcaggcga ccttggctgg cggctcagcc tgttgctgct acccttgctt      60
ctggtacaag ctggttcctg ggggttccca acagaccccc tgagccttca agagctgcgc     120
agggaattca cagtcagcct gtaccttgcc aggaagctgc tctctgaggt tcagggctat     180
gtccacagct ttgctgaatc tcgattgcca ggagtgaacc tggacctcct gcccctggga     240
taccatcttc ccaatgtttc cctgactttc caggcatggc atcacctctc tgactctgag     300
agactctgct cctcgctac cacacttcgg cccttccctg ccatgctggg agggctgggg     360
acccagggga cctggaccag ctcagagagg gagcagctgt gggccatgag gctggatctc     420
```

```
cgggacctgc acaggcacct ccgctttcag gtgctggctg caggattcaa atgttcaaag      480
gaggaggagg acaaggagga agaggaagag gaggaagaag aagaaaagaa gctgccccta      540
ggggctctgg gtggcccccaa tcaggtgtca tcccaagtgt cctggcccca gctgctctat     600
acctaccagc tccttcactc cctggagctt gtcctgtctc gggctgttcg ggacctgctg      660
ctgctgtccc tgcccaggcg cccaggctca gcctgggatt cctaacacct agcttcaagc      720
cctatggagt gaccttccag ctccctccct cgcccgttaa gactctaagg ctggagtctg      780
gccaatcaca ggacaggctc tagctcgttt gccttagacc aggcagggct tcactagctc      840
ccagccctga cccaataatt taaaagccct ccagtcctta ccagatattt atttcttgga      900
tatttattta ttttaagaa atggtttatt tattgtttca ctcttgagtt aggccaccat       960
gctgggtgcc taataaagcc atccagcccg g                                    991
```

```
<210> SEQ ID NO 8
<211> LENGTH: 234
<212> TYPE: PRT
<213> ORGANISM: Mus musculus

<400> SEQUENCE: 8

Met Gly Gln Thr Ala Gly Asp Leu Gly Trp Arg Leu Ser Leu Leu Leu
1               5                   10                  15

Leu Pro Leu Leu Leu Val Gln Ala Gly Ser Trp Gly Phe Pro Thr Asp
            20                  25                  30

Pro Leu Ser Leu Gln Glu Leu Arg Arg Glu Phe Thr Val Ser Leu Tyr
        35                  40                  45

Leu Ala Arg Lys Leu Leu Ser Glu Val Gln Gly Tyr Val His Ser Phe
    50                  55                  60

Ala Glu Ser Arg Leu Pro Gly Val Asn Leu Asp Leu Pro Leu Gly
65                  70                  75                  80

Tyr His Leu Pro Asn Val Ser Leu Thr Phe Gln Ala Trp His His Leu
                85                  90                  95

Ser Asp Ser Glu Arg Leu Cys Phe Leu Ala Thr Thr Leu Arg Pro Phe
            100                 105                 110

Pro Ala Met Leu Gly Gly Leu Gly Thr Gln Gly Thr Trp Thr Ser Ser
        115                 120                 125

Glu Arg Glu Gln Leu Trp Ala Met Arg Leu Asp Leu Arg Asp Leu His
    130                 135                 140

Arg His Leu Arg Phe Gln Val Leu Ala Ala Gly Phe Lys Cys Ser Lys
145                 150                 155                 160

Glu Glu Glu Asp Lys Glu Glu Glu Glu Glu Glu Glu Glu Glu Glu Lys
                165                 170                 175

Lys Leu Pro Leu Gly Ala Leu Gly Gly Pro Asn Gln Val Ser Ser Gln
            180                 185                 190

Val Ser Trp Pro Gln Leu Leu Tyr Thr Tyr Gln Leu Leu His Ser Leu
        195                 200                 205

Glu Leu Val Leu Ser Arg Ala Val Arg Asp Leu Leu Leu Ser Leu
    210                 215                 220

Pro Arg Arg Pro Gly Ser Ala Trp Asp Ser
225                 230

<210> SEQ ID NO 9
<211> LENGTH: 1161
<212> TYPE: DNA
<213> ORGANISM: Homo sapiens
```

```
<220> FEATURE:
<221> NAME/KEY: CDS
<222> LOCATION: (14)..(700)
<223> OTHER INFORMATION:

<400> SEQUENCE: 9
gaattccgca gcc atg acc ccg cag ctt ctc ctg gcc ctt gtc ctc tgg         49
           Met Thr Pro Gln Leu Leu Leu Ala Leu Val Leu Trp
            1               5                  10 gcc agc tgc ccg ccc tgc agt gga agg aaa ggg ccc cca gca gct ctg        97
Ala Ser Cys Pro Pro Cys Ser Gly Arg Lys Gly Pro Pro Ala Ala Leu
        15                  20                  25 aca ctg ccc cgg gtg caa tgc cga gcc tct cgg tac ccg atc gcc gtg       145
Thr Leu Pro Arg Val Gln Cys Arg Ala Ser Arg Tyr Pro Ile Ala Val
 30                  35                  40 gat tgc tcc tgg acc ctg ccg cct gct cca aac tcc acc agc ccc gtg       193
Asp Cys Ser Trp Thr Leu Pro Pro Ala Pro Asn Ser Thr Ser Pro Val
 45              50                  55                  60 tcc ttc att gcc acg tac agg ctc ggc atg gct gcc cgg ggc cac agc       241
Ser Phe Ile Ala Thr Tyr Arg Leu Gly Met Ala Ala Arg Gly His Ser
                 65                  70                  75 tgg ccc tgc ctg cag cag acg cca acg tcc acc agc tgc acc atc acg       289
Trp Pro Cys Leu Gln Gln Thr Pro Thr Ser Thr Ser Cys Thr Ile Thr
             80                  85                  90 gat gtc cag ctg ttc tcc atg gct ccc tac gtg ctc aat gtc acc gcc       337
Asp Val Gln Leu Phe Ser Met Ala Pro Tyr Val Leu Asn Val Thr Ala
         95                 100                 105 gtc cac ccc tgg ggc tcc agc agc agc ttc gtg cct ttc ata aca gag       385
Val His Pro Trp Gly Ser Ser Ser Ser Phe Val Pro Phe Ile Thr Glu
    110                 115                 120 cac atc atc aag ccc gac cct cca gaa ggc gtg cgc cta agc ccc ctc       433
His Ile Ile Lys Pro Asp Pro Pro Glu Gly Val Arg Leu Ser Pro Leu
125                 130                 135                 140 gct gag cgc cac gta cag gtg cag tgg gag cct ccc ggg tcc tgg ccc       481
Ala Glu Arg His Val Gln Val Gln Trp Glu Pro Pro Gly Ser Trp Pro
                145                 150                 155 ttc cca gag atc ttc tca ctg aag tac tgg atc cgt tac aag cgt cag       529
Phe Pro Glu Ile Phe Ser Leu Lys Tyr Trp Ile Arg Tyr Lys Arg Gln
            160                 165                 170 gga gct gcg cgc ttc cac cgg gtg ggg ccc att gaa gcc acg tcc ttc       577
Gly Ala Ala Arg Phe His Arg Val Gly Pro Ile Glu Ala Thr Ser Phe
        175                 180                 185 atc ctc agg gct gtg cgg ccc cga gcc agg tac tac gtc caa gtg gcg       625
Ile Leu Arg Ala Val Arg Pro Arg Ala Arg Tyr Tyr Val Gln Val Ala
    190                 195                 200 gct cag gac ctc aca gac tac ggg gaa ctg agt gac tgg agt ctc ccc       673
Ala Gln Asp Leu Thr Asp Tyr Gly Glu Leu Ser Asp Trp Ser Leu Pro
205                 210                 215                 220 gcc act gcc aca atg agc ctg ggc aag tagcaagggc ttcccgctgc             720
Ala Thr Ala Thr Met Ser Leu Gly Lys
                225 ctccagacag cacctgggtc ctcgccaccc taagccccgg acacctgtt ggagggcgga      780 tgggatctgc ctagcctggg ctggagtcct tgctttgctg ctgctgagct gccgggcaac     840 ctcagatgac cgactttttcc ctttgagcct cagtttctct agctgagaaa tggagatgta    900 ctactctctc ctttaccttt acctttacca cagtgcaggg ctgactgaac tgtcactgtg     960 agatattttt tattgtttaa ttagaaaaga attgttgttg ggctgggcgc agtggatcgc    1020 acctgtaatc ccagtcactg ggaagccgac gtgggtgggt agcttgaggc caggagctcg   1080
```

-continued

```
aaaccagtcc gggccacaca gcaagacccc atctctaaaa aattaatata aatataaaat    1140
aaaaaaaaaa aaaaggaatt c                                              1161
```

<210> SEQ ID NO 10
<211> LENGTH: 229
<212> TYPE: PRT
<213> ORGANISM: Homo sapiens

<400> SEQUENCE: 10

```
Met Thr Pro Gln Leu Leu Leu Ala Leu Val Leu Trp Ala Ser Cys Pro
1               5                   10                  15

Pro Cys Ser Gly Arg Lys Gly Pro Ala Ala Leu Thr Leu Pro Arg
            20                  25                  30

Val Gln Cys Arg Ala Ser Arg Tyr Pro Ile Ala Val Asp Cys Ser Trp
        35                  40                  45

Thr Leu Pro Pro Ala Pro Asn Ser Thr Ser Pro Val Ser Phe Ile Ala
    50                  55                  60

Thr Tyr Arg Leu Gly Met Ala Ala Arg Gly His Ser Trp Pro Cys Leu
65                  70                  75                  80

Gln Gln Thr Pro Thr Ser Thr Ser Cys Thr Ile Thr Asp Val Gln Leu
                85                  90                  95

Phe Ser Met Ala Pro Tyr Val Leu Asn Val Thr Ala Val His Pro Trp
            100                 105                 110

Gly Ser Ser Ser Phe Val Pro Phe Ile Thr Glu His Ile Ile Lys
        115                 120                 125

Pro Asp Pro Pro Glu Gly Val Arg Leu Ser Pro Leu Ala Glu Arg His
    130                 135                 140

Val Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
            180                 185                 190

Val Arg Pro Arg Ala Arg Tyr Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225
```

<210> SEQ ID NO 11
<211> LENGTH: 2628
<212> TYPE: DNA
<213> ORGANISM: Homo sapiens
<220> FEATURE:
<221> NAME/KEY: CDS
<222> LOCATION: (112)..(2019)
<223> OTHER INFORMATION:
<220> FEATURE:
<221> NAME/KEY: misc_feature
<222> LOCATION: (2433)..(2433)
<223> OTHER INFORMATION: Unidentified base.

-continued

```
<400> SEQUENCE: 11
gtgggttcgg cttcccgttg cgcctcgggg gctgtaccca gagctcgaag aggagcagcg      60
cggcccgcac ccggcaaggc tgggccggac tcggggctcc cgagggacgc c atg cgg     117
                                                          Met Arg
                                                            1 gga ggc agg ggc ggc cct ttc tgg ctg tgg ccg ctg ccc aag ctg gcg      165
Gly Gly Arg Gly Gly Pro Phe Trp Leu Trp Pro Leu Pro Lys Leu Ala
        5                  10                  15 ctg ctg cct ctg ttg tgg gtg ctt ttc cag cgg acg cgt ccc cag ggc      213
Leu Leu Pro Leu Leu Trp Val Leu Phe Gln Arg Thr Arg Pro Gln Gly
 20                  25                  30 agc gcc ggg cca ctg cag tgc tac gga gtt gga ccc ttg ggc gac ttg      261
Ser Ala Gly Pro Leu Gln Cys Tyr Gly Val Gly Pro Leu Gly Asp Leu
 35              40                  45                  50 aac tgc tcg tgg gag cct ctt ggg gac ctg gga gcc ccc tcc gag tta      309
Asn Cys Ser Trp Glu Pro Leu Gly Asp Leu Gly Ala Pro Ser Glu Leu
                 55                  60                  65 cac ctc cag agc caa aag tac cgt tcc aac aaa acc cag act gtg gca      357
His Leu Gln Ser Gln Lys Tyr Arg Ser Asn Lys Thr Gln Thr Val Ala
             70                  75                  80 gtg gca gcc gga cgg agc tgg gtg gcc att cct cgg gaa cag ctc acc      405
Val Ala Ala Gly Arg Ser Trp Val Ala Ile Pro Arg Glu Gln Leu Thr
         85                  90                  95 atg tct gac aaa ctc ctt gtc tgg ggc act aag gca ggc cag cct ctc      453
Met Ser Asp Lys Leu Leu Val Trp Gly Thr Lys Ala Gly Gln Pro Leu
    100                 105                 110 tgg ccc ccc gtc ttc gtg aac cta gaa acc caa atg aag cca aac gcc      501
Trp Pro Pro Val Phe Val Asn Leu Glu Thr Gln Met Lys Pro Asn Ala
115                 120                 125                 130 ccc cgg ctg ggc cct gac gtg gac ttt tcc gag gat gac ccc ctg gag      549
Pro Arg Leu Gly Pro Asp Val Asp Phe Ser Glu Asp Asp Pro Leu Glu
                135                 140                 145 gcc act gtc cat tgg gcc cca cct aca tgg cca tct cat aaa gtt ctg      597
Ala Thr Val His Trp Ala Pro Pro Thr Trp Pro Ser His Lys Val Leu
            150                 155                 160 atc tgc cag ttc cac tac cga aga tgt cag gag gcg gcc tgg acc ctg      645
Ile Cys Gln Phe His Tyr Arg Arg Cys Gln Glu Ala Ala Trp Thr Leu
        165                 170                 175 ctg gaa ccg gag ctg aag acc ata ccc ctg acc cct gtt gag atc caa      693
Leu Glu Pro Glu Leu Lys Thr Ile Pro Leu Thr Pro Val Glu Ile Gln
    180                 185                 190 gat ttg gag cta gcc act ggc tac aaa gtg tat ggc cgc tgc cgg atg      741
Asp Leu Glu Leu Ala Thr Gly Tyr Lys Val Tyr Gly Arg Cys Arg Met
195                 200                 205                 210 gag aaa gaa gag gat ttg tgg ggc gag tgg agc ccc att ttg tcc ttc      789
Glu Lys Glu Glu Asp Leu Trp Gly Glu Trp Ser Pro Ile Leu Ser Phe
                215                 220                 225 cag aca ccg cct tct gct cca aaa gat gtg tgg gta tca ggg aac ctc      837
Gln Thr Pro Pro Ser Ala Pro Lys Asp Val Trp Val Ser Gly Asn Leu
            230                 235                 240 tgt ggg acg cct gga gga gag gaa cct ttg ctt cta tgg aag gcc cca      885
Cys Gly Thr Pro Gly Gly Glu Glu Pro Leu Leu Leu Trp Lys Ala Pro
        245                 250                 255 ggg ccc tgt gtg cag gtg agc tac aaa gtc tgg ttc tgg gtt gga ggt      933
Gly Pro Cys Val Gln Val Ser Tyr Lys Val Trp Phe Trp Val Gly Gly
    260                 265                 270 cgt gag ctg agt cca gaa gga att acc tgc tgc tgc tcc cta att ccc      981
Arg Glu Leu Ser Pro Glu Gly Ile Thr Cys Cys Cys Ser Leu Ile Pro
275                 280                 285                 290
```

```
agt ggg gcg gag tgg gcc agg gtg tcc gct gtc aac gcc aca agc tgg    1029
Ser Gly Ala Glu Trp Ala Arg Val Ser Ala Val Asn Ala Thr Ser Trp
            295                 300                 305 gag cct ctc acc aac ctc tct ttg gtc tgc ttg gat tca gcc tct gcc    1077
Glu Pro Leu Thr Asn Leu Ser Leu Val Cys Leu Asp Ser Ala Ser Ala
        310                 315                 320 ccc cgt agc gtg gca gtc agc agc atc gct ggg agc acg gag cta ctg    1125
Pro Arg Ser Val Ala Val Ser Ser Ile Ala Gly Ser Thr Glu Leu Leu
        325                 330                 335 gtg acc tgg caa ccg ggg cct ggg gaa cca ctg gag cat gta gtg gac    1173
Val Thr Trp Gln Pro Gly Pro Gly Glu Pro Leu Glu His Val Val Asp
    340                 345                 350 tgg gct cga gat ggg gac ccc ctg gag aaa ctc aac tgg gtc cgg ctt    1221
Trp Ala Arg Asp Gly Asp Pro Leu Glu Lys Leu Asn Trp Val Arg Leu
355                 360                 365                 370 ccc cct ggg aac ctc agt gct ctg tta cca ggg aat ttc act gtc ggg    1269
Pro Pro Gly Asn Leu Ser Ala Leu Leu Pro Gly Asn Phe Thr Val Gly
            375                 380                 385 gtc ccc tat cga atc act gtg acc gca gtc tct gct tca ggc ttg gcc    1317
Val Pro Tyr Arg Ile Thr Val Thr Ala Val Ser Ala Ser Gly Leu Ala
        390                 395                 400 tct gca tcc tcc gtc tgg ggg ttc agg gag gaa tta gca ccc cta gtg    1365
Ser Ala Ser Ser Val Trp Gly Phe Arg Glu Glu Leu Ala Pro Leu Val
        405                 410                 415 ggg cca acg ctt tgg cga ctc caa gat gcc cct cca ggg acc ccc gcc    1413
Gly Pro Thr Leu Trp Arg Leu Gln Asp Ala Pro Pro Gly Thr Pro Ala
    420                 425                 430 ata gcg tgg gga gag gtc cca agg cac cag ctt cga ggc cac ctc acc    1461
Ile Ala Trp Gly Glu Val Pro Arg His Gln Leu Arg Gly His Leu Thr
435                 440                 445                 450 cac tac acc ttg tgt gca cag agt gga acc agc ccc tcc gtc tgc atg    1509
His Tyr Thr Leu Cys Ala Gln Ser Gly Thr Ser Pro Ser Val Cys Met
            455                 460                 465 aat gtg agt ggc aac aca cag agt gtc acc ctg cct gac ctt cct tgg    1557
Asn Val Ser Gly Asn Thr Gln Ser Val Thr Leu Pro Asp Leu Pro Trp
        470                 475                 480 ggt ccc tgt gag ctg tgg gtg aca gca tct acc atc gct gga cag ggc    1605
Gly Pro Cys Glu Leu Trp Val Thr Ala Ser Thr Ile Ala Gly Gln Gly
        485                 490                 495 cct cct ggt ccc atc ctc cgg ctt cat cta cca gat aac acc ctg agg    1653
Pro Pro Gly Pro Ile Leu Arg Leu His Leu Pro Asp Asn Thr Leu Arg
    500                 505                 510 tgg aaa gtt ctg ccg ggc atc cta ttc ttg tgg ggc ttg ttc ctg ttg    1701
Trp Lys Val Leu Pro Gly Ile Leu Phe Leu Trp Gly Leu Phe Leu Leu
515                 520                 525                 530 ggg tgt ggc ctg agc ctg gcc acc tct gga agg tgc tac cac cta agg    1749
Gly Cys Gly Leu Ser Leu Ala Thr Ser Gly Arg Cys Tyr His Leu Arg
            535                 540                 545 cac aaa gtg ctg ccc cgc tgg gtc tgg gag aaa gtt cct gat cct gcc    1797
His Lys Val Leu Pro Arg Trp Val Trp Glu Lys Val Pro Asp Pro Ala
        550                 555                 560 aac agc agt tca ggc cag ccc cac atg gag caa gta cct gag gcc cag    1845
Asn Ser Ser Ser Gly Gln Pro His Met Glu Gln Val Pro Glu Ala Gln
        565                 570                 575 ccc ctt ggg gac ttg ccc atc ctg gaa gtg gag gag atg gag ccc ccg    1893
Pro Leu Gly Asp Leu Pro Ile Leu Glu Val Glu Glu Met Glu Pro Pro
    580                 585                 590 ccg gtt atg gag tcc tcc cag ccc gcc cag gcc acc gcc ccg ctt gac    1941
Pro Val Met Glu Ser Ser Gln Pro Ala Gln Ala Thr Ala Pro Leu Asp
595                 600                 605                 610
```

```
                                              -continued
tct ggg tat gag aag cac ttc ctg ccc aca cct gag gag ctg ggc ctt        1989
Ser Gly Tyr Glu Lys His Phe Leu Pro Thr Pro Glu Glu Leu Gly Leu
                615                 620                 625 ctg ggg ccc ccc agg cca cag gtt ctg gcc tgaaccacac gtctggctgg         2039
Leu Gly Pro Pro Arg Pro Gln Val Leu Ala
    630                 635 gggctgccag ccaggctaga gggatgctca tgcaggttgc accccagtcc tggattagcc     2099
ctcttgatgg atgaagacac tgaggactca gagaggctga gtcacttacc tgaggacacc     2159
cagccaggca gagctgggat tgaaggaccc ctatagagaa gggcttggcc cccatgggga     2219
agacacggat ggaaggtgga gcaaaggaaa atacatgaaa ttgagagtgg cagctgcctg     2279
ccaaaatctg ttccgctgta acagaactga atttggaccc cagcacagtg gctcacgcct     2339
gtaatcccag cactttggca ggccaaggtg aaggatcac ttagagctag gagtttgaga      2399
ccagcctggg caatatagca agacccctca ctanaaaaat aaaacatcaa aaacaaaaac     2459
aattagctgg gcatgatggc acacacctgt agtccgagcc acttgggagg ctgaggtggg     2519
aggatcggtt gagcccagga gttcgaagct gcagggacct ctgattgcac cactgcactc     2579
caggctgggt aacagaatga gaccttatct caaaaataaa caaactaat                 2628

<210> SEQ ID NO 12
<211> LENGTH: 636
<212> TYPE: PRT
<213> ORGANISM: Homo sapiens
<220> FEATURE:
<221> NAME/KEY: misc_feature
<222> LOCATION: (2433)..(2433)
<223> OTHER INFORMATION: Unidentified base.

<400> SEQUENCE: 12

Met Arg Gly Gly Arg Gly Gly Pro Phe Trp Leu Trp Pro Leu Pro Lys
1               5                   10                  15

Leu Ala Leu Leu Pro Leu Leu Trp Val Leu Phe Gln Arg Thr Arg Pro
            20                  25                  30

Gln Gly Ser Ala Gly Pro Leu Gln Cys Tyr Gly Val Gly Pro Leu Gly
        35                  40                  45

Asp Leu Asn Cys Ser Trp Glu Pro Leu Gly Asp Leu Gly Ala Pro Ser
    50                  55                  60

Glu Leu His Leu Gln Ser Gln Lys Tyr Arg Ser Asn Lys Thr Gln Thr
65                  70                  75                  80

Val Ala Val Ala Ala Gly Arg Ser Trp Val Ala Ile Pro Arg Glu Gln
                85                  90                  95

Leu Thr Met Ser Asp Lys Leu Leu Val Trp Gly Thr Lys Ala Gly Gln
            100                 105                 110

Pro Leu Trp Pro Pro Val Phe Val Asn Leu Glu Thr Gln Met Lys Pro
        115                 120                 125

Asn Ala Pro Arg Leu Gly Pro Asp Val Asp Phe Ser Glu Asp Asp Pro
    130                 135                 140

Leu Glu Ala Thr Val His Trp Ala Pro Pro Thr Trp Pro Ser His Lys
145                 150                 155                 160

Val Leu Ile Cys Gln Phe His Tyr Arg Arg Cys Gln Glu Ala Ala Trp
                165                 170                 175

Thr Leu Leu Glu Pro Glu Leu Lys Thr Ile Pro Leu Thr Pro Val Glu
            180                 185                 190

Ile Gln Asp Leu Glu Leu Ala Thr Gly Tyr Lys Val Tyr Gly Arg Cys
        195                 200                 205
```

```
Arg Met Glu Lys Glu Glu Asp Leu Trp Gly Glu Trp Ser Pro Ile Leu
    210                 215                 220

Ser Phe Gln Thr Pro Pro Ser Ala Pro Lys Asp Val Trp Val Ser Gly
225                 230                 235                 240

Asn Leu Cys Gly Thr Pro Gly Gly Glu Glu Pro Leu Leu Leu Trp Lys
                245                 250                 255

Ala Pro Gly Pro Cys Val Gln Val Ser Tyr Lys Val Trp Phe Trp Val
            260                 265                 270

Gly Gly Arg Glu Leu Ser Pro Glu Gly Ile Thr Cys Cys Cys Ser Leu
        275                 280                 285

Ile Pro Ser Gly Ala Glu Trp Ala Arg Val Ser Ala Val Asn Ala Thr
    290                 295                 300

Ser Trp Glu Pro Leu Thr Asn Leu Ser Leu Val Cys Leu Asp Ser Ala
305                 310                 315                 320

Ser Ala Pro Arg Ser Val Ala Val Ser Ser Ile Ala Gly Ser Thr Glu
                325                 330                 335

Leu Leu Val Thr Trp Gln Pro Gly Pro Gly Glu Pro Leu Glu His Val
            340                 345                 350

Val Asp Trp Ala Arg Asp Gly Asp Pro Leu Glu Lys Leu Asn Trp Val
        355                 360                 365

Arg Leu Pro Pro Gly Asn Leu Ser Ala Leu Leu Pro Gly Asn Phe Thr
    370                 375                 380

Val Gly Val Pro Tyr Arg Ile Thr Val Thr Ala Val Ser Ala Ser Gly
385                 390                 395                 400

Leu Ala Ser Ala Ser Ser Val Trp Gly Phe Arg Glu Glu Leu Ala Pro
                405                 410                 415

Leu Val Gly Pro Thr Leu Trp Arg Leu Gln Asp Ala Pro Pro Gly Thr
            420                 425                 430

Pro Ala Ile Ala Trp Gly Glu Val Pro Arg His Gln Leu Arg Gly His
        435                 440                 445

Leu Thr His Tyr Thr Leu Cys Ala Gln Ser Gly Thr Ser Pro Ser Val
    450                 455                 460

Cys Met Asn Val Ser Gly Asn Thr Gln Ser Val Thr Leu Pro Asp Leu
465                 470                 475                 480

Pro Trp Gly Pro Cys Glu Leu Trp Val Thr Ala Ser Thr Ile Ala Gly
                485                 490                 495

Gln Gly Pro Pro Gly Pro Ile Leu Arg Leu His Leu Pro Asp Asn Thr
            500                 505                 510

Leu Arg Trp Lys Val Leu Pro Gly Ile Leu Phe Leu Trp Gly Leu Phe
        515                 520                 525

Leu Leu Gly Cys Gly Leu Ser Leu Ala Thr Ser Gly Arg Cys Tyr His
    530                 535                 540

Leu Arg His Lys Val Leu Pro Arg Trp Val Trp Glu Lys Val Pro Asp
545                 550                 555                 560

Pro Ala Asn Ser Ser Gly Gln Pro His Met Glu Gln Val Pro Glu
                565                 570                 575

Ala Gln Pro Leu Gly Asp Leu Pro Ile Leu Glu Val Glu Glu Met Glu
            580                 585                 590

Pro Pro Pro Val Met Glu Ser Ser Gln Pro Ala Gln Ala Thr Ala Pro
        595                 600                 605
```

-continued

```
Leu Asp Ser Gly Tyr Glu Lys His Phe Leu Pro Thr Pro Glu Glu Leu
    610                 615                 620
Gly Leu Leu Gly Pro Pro Arg Pro Gln Val Leu Ala
625                 630                 635

<210> SEQ ID NO 13
<211> LENGTH: 15
<212> TYPE: PRT
<213> ORGANISM: Synthetic.

<400> SEQUENCE: 13

Gly Ser Gly Ser Gly Gly Ser Gly Gly Ser Gly Ser Gly Lys Leu
1               5                   10                  15
```